US010751019B2

(12) United States Patent
Matthews et al.

(10) Patent No.: US 10,751,019 B2
(45) Date of Patent: Aug. 25, 2020

(54) DETERMINING A BRAIN CONDITION USING EARLY TIME FRAME PET IMAGE ANALYSIS

(71) Applicant: ADM DIAGNOSTICS, LLC, Skokie, IL (US)

(72) Inventors: Dawn C. Matthews, Grayslake, IL (US); Ana S. Lukic, Chicago, IL (US); Randolph D. Andrews, McHenry, IL (US); Miles N. Wernick, Evanston, IL (US); Stephen C. Strother, Toronto (CA)

(73) Assignee: ADM DIAGNOSTICS, INC., Skokie, IL (US)

( * ) Notice: Subject to any disclaimer, the term of this patent is extended or adjusted under 35 U.S.C. 154(b) by 0 days.

(21) Appl. No.: 15/760,391

(22) PCT Filed: Sep. 15, 2016

(86) PCT No.: PCT/US2016/051854
§ 371 (c)(1),
(2) Date: Mar. 15, 2018

(87) PCT Pub. No.: WO2017/048904
PCT Pub. Date: Mar. 23, 2017

(65) Prior Publication Data
US 2018/0256127 A1    Sep. 13, 2018

Related U.S. Application Data

(60) Provisional application No. 62/219,421, filed on Sep. 16, 2015.

(51) Int. Cl.
*A61B 6/00*    (2006.01)
*A61B 6/03*    (2006.01)
(Continued)

(52) U.S. Cl.
CPC ............ *A61B 6/5217* (2013.01); *A61B 5/055* (2013.01); *A61B 5/4064* (2013.01);
(Continued)

(58) Field of Classification Search
CPC ..... A61B 6/5217; A61B 5/055; A61B 5/4064; A61B 5/4088
See application file for complete search history.

(56) References Cited

U.S. PATENT DOCUMENTS 8,620,046 B2 * 12/2013 Nagler .................... A61B 6/00
  382/128
2002/0186875 A1    12/2002 Burmer et al.
(Continued)

FOREIGN PATENT DOCUMENTS

WO    2014195448 A1    12/2014

OTHER PUBLICATIONS

Chien, David T. "Early Clinical PET Imaging Results with the NovelPHF-Tau Radiogland" Journal of Alzheimer's Disease 38 (2014). (Year: 2014).*

(Continued)

*Primary Examiner* — Kim Y Vu
*Assistant Examiner* — Molly Delaney
(74) *Attorney, Agent, or Firm* — Quarles & Brady LLP

(57) ABSTRACT

Systems and methods for use in identifying a brain condition of a subject are provided. In some aspects, a provided method includes constructing a classifier to identify a brain condition of a subject comprising steps of receiving image data obtained from a plurality of subjects, wherein the image data is acquired during an acquisition period following administration of at least one radioactive tracer. The method also includes defining a plurality of brain condition classes using the image data associated with one or more time frames during the acquisition period, and processing the (Continued)

Amyloid negative scan

Amyloid positive scan image data to generate signatures corresponding to each of the plurality brain condition classes. The method further includes constructing the classifier using the signatures. The classifier can then be applied to determine a degree to which the subject expresses one or more disease states in order to determine a brain condition of the subject.

26 Claims, 24 Drawing Sheets

(51) Int. Cl.
    *A61B 5/00*     (2006.01)
    *A61B 5/055*     (2006.01)
    *G16H 50/20*     (2018.01)
    *G16H 30/40*     (2018.01)
    *G06K 9/62*     (2006.01)
    *G06T 7/00*     (2017.01)

(52) U.S. Cl.
    CPC .......... *A61B 5/4088* (2013.01); *A61B 5/7267* (2013.01); *A61B 6/037* (2013.01); *A61B 6/486* (2013.01); *A61B 6/501* (2013.01); *G06K 9/627* (2013.01); *G06K 9/6257* (2013.01); *G06T 7/0016* (2013.01); *G16H 30/40* (2018.01); *G16H 50/20* (2018.01); *G06K 2209/05* (2013.01); *G06T 2207/10104* (2013.01); *G06T 2207/10108* (2013.01); *G06T 2207/20081* (2013.01); *G06T 2207/30016* (2013.01)

(56) References Cited

U.S. PATENT DOCUMENTS

| | | | |
|---|---|---|---|
| 2008/0074649 A1 | 3/2008 | Levenson et al. | |
| 2008/0137969 A1* | 6/2008 | Rueckert | G06K 9/6234 382/224 |
| 2008/0310697 A1* | 12/2008 | Razifar | G06T 5/002 382/131 |
| 2010/0135556 A1* | 6/2010 | Razifar | G06T 7/12 382/131 |
| 2010/0142786 A1* | 6/2010 | Degani | A61B 5/055 382/131 |
| 2010/0179415 A1 | 7/2010 | Wenzel et al. | |
| 2010/0183202 A1* | 7/2010 | Takahashi | A61B 5/7267 382/128 |
| 2012/0232381 A1 | 9/2012 | Gilhuijs et al. | |
| 2017/0220900 A1* | 8/2017 | Boada | A61B 5/0042 |
| 2019/0026888 A1* | 1/2019 | Beveridge | G06T 11/00 |
| 2019/0114766 A1* | 4/2019 | Song | G06T 7/0012 |
| 2019/0129026 A1* | 5/2019 | Sumi | G01S 13/90 |

OTHER PUBLICATIONS

Lim, Hyun Kook "Regional amyloid burden and intrinsic connectivitynetworks in cognitively normal elderly subjects" Brain Journal of Neurology. (Year: 2014).*

European Patent Office, Extended European Search Report, Application No. 16847270.2, dated Apr. 23, 2019, 8 pages.

International Search Report and Written Opinion for International Patent Application No. PCT/US2016/051854 dated Sep. 15, 2016.

* cited by examiner

Dementia Differentiation Class Examples

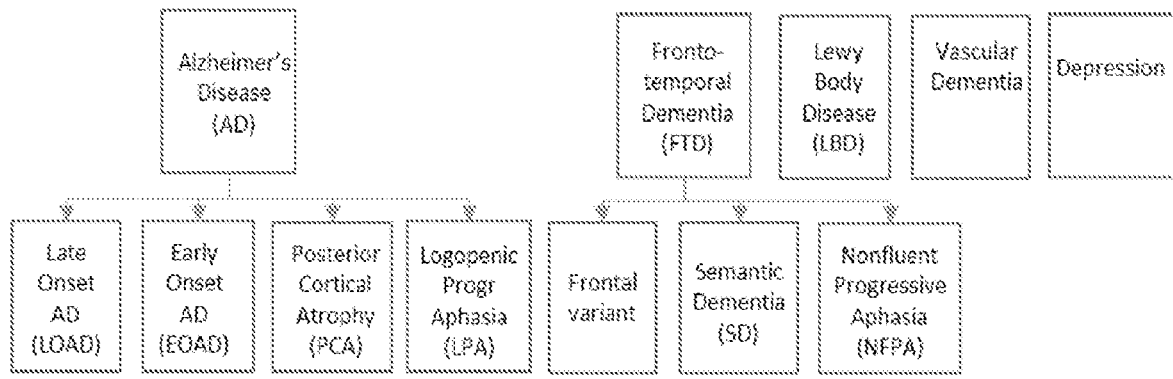

Alzheimer's Progression Class Examples (Am+ = amyloid positive; Am- = amyloid negative; cAD = converted to AD; * = may be used as test class only)

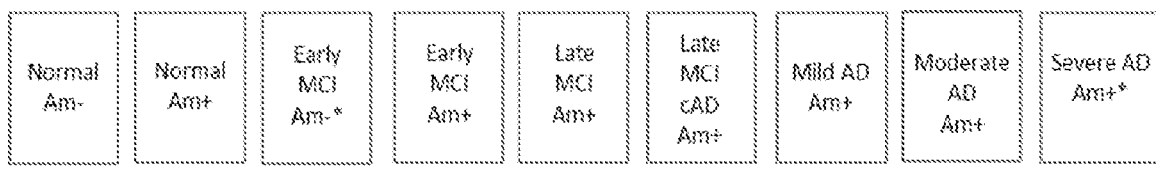

Amyloid Burden Progression (florbetapir example, based upon late timeframe ("standard") SUVR values; thr = threshold)

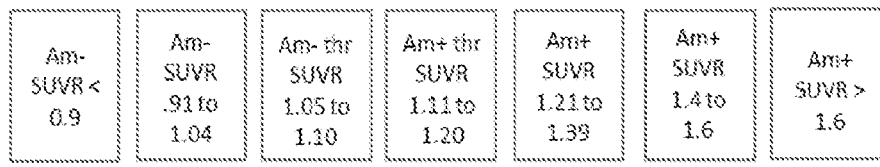

Example of Assignment of Discrete Frames to Classes (example if scans are 20 minutes in 5 timeframes)
5 diagnostic classes becomes 25 (5 classes x 5 timeframes) classes.

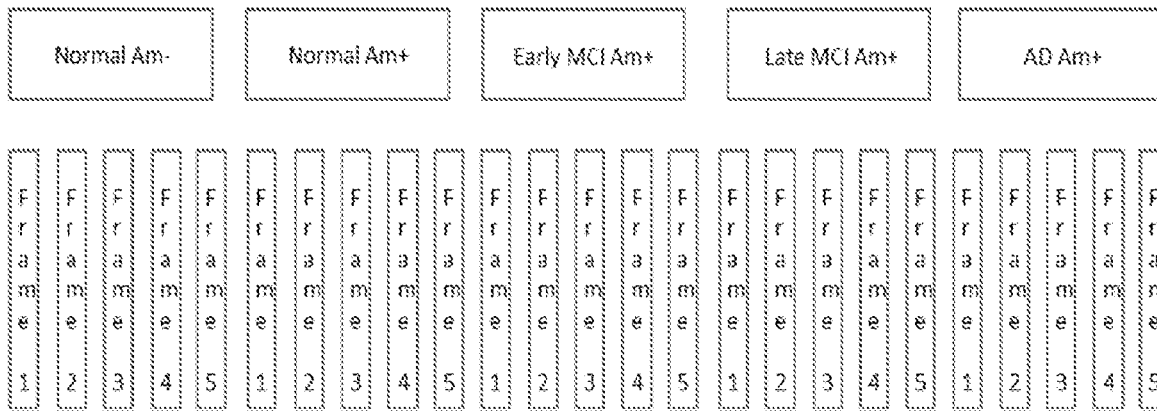

FIG. 5

DETERMINING A BRAIN CONDITION USING EARLY TIME FRAME PET IMAGE ANALYSIS

CROSS-REFERENCE TO RELATED APPLICATIONS

This application represents the national stage entry of PCT International Application No. PCT/US2016/051854 filed on Sep. 15, 2016 and claims the benefit of, is based on, and incorporates herein by reference in its entirety U.S. Provisional Patent Application Ser. No. 62/219,421 filed on Sep. 16, 2015 and entitled "SYSTEMS AND METHODS FOR DETERMINING A BRAIN CONDITION OF A SUBJECT USING EARLY FRAME PET IMAGE ANALYSIS."

BACKGROUND

The present disclosure relates generally to systems and methods for determining a medical condition of a patient using imaging data and, in particular, to systems and methods for identifying the presence and/or progression of a brain condition of a subject.

Neurodegenerative diseases and other syndromes affecting the brain commonly exhibit distinctive symptoms and characteristics that often become more pronounced as disease severity increases. During diagnosis, specific signatures visible on various imaging modalities are utilized to determine the presence and state of the disease. For instance, with glucose being a primary source of energy for neuronal activity, measurement of glucose metabolism using positron emission tomography ("PET") imaging has been demonstrated to provide measures of neuronal decline in affected brain areas for a variety of neurodegenerative diseases and syndromes. Similarly, as neurons degrade, brain volume decreases according to characteristic patterns, which is measurable using magnetic resonance imaging ("MRI"). Other imaging modalities, such as functional MRI and single photon emission computed tomography ("SPECT"), as well as other biomarkers, including imaging amyloid plaques and tangles, have also been used to measure brain function for diagnosing and treating neurodegenerative diseases.

PET imaging technology measures chemical or functional activity in the brain by detecting gamma rays emitted by the decay of radioactive tracers injected into a patient. The greater the amount of the target of interest, the greater the binding of the tracer to that target, and the hence greater and more pervasive the signal intensity detected. Various tracers have been developed that bind to different targets in the brain, such as neurotransmitter receptors or amyloid plaque. For instance, common tracers used for imaging amyloid plaques include 11C-PiB (Pittsburgh Compound B), florbetapir (Lilly/Avid), flutemetamol (GE Healthcare), florbetaben (Piramal), and others.

In patients with Alzheimer's Disease ("AD"), amyloid plaque is the result of accumulation of abnormally cleaved proteins that cluster together outside nerve cells or neurons, leading to disruptions in neural communication and function, as well as cell death. Therefore, the presence of amyloid plaques is part of the diagnostic criteria for AD, and amyloid imaging has been incorporated into many clinical trials. As an example, FIGS. 1A and 1B show transaxial and sagittal amyloid PET images from two different patients, illustrating different radiotracer activity patterns in the brain. In particular, FIG. 1A shows an amyloid negative scan, while FIG. 1B shows an amyloid positive scan, as visible from the increased signal intensities relative to FIG. 1A. In general, amyloid plaque accumulates in gray matter ("GM") regions, as indicated by arrows 100 in the positive scan of FIG. 1B. However, many amyloid PET tracers can also bind to white matter ("WM") as well, as appreciated by non-specific white matter binding around the ventricles in the middle of the brain in FIGS. 1A and 1B, and indicated by arrows 102. This may be due either to slower clearance of the tracer from WM, non-specific binding to WM, or specific binding to a non-amyloid entity such as myelin. Hence, specific binding to amyloid in gray matter tissue in the amyloid-positive Data collected by a PET scanner can be assembled into a series of images or frames, each representing radioactivity detected over a specific time window after tracer administration. The duration of each window may depend on the time elapsed from tracer injection. For instance, early images obtained shortly following radiotracer injection may be acquired over windows lasting a few seconds in order to capture rapid changes in emitted signal, while later images can be acquired over windows lasting from several minutes up to 30 minutes or even longer. In some cases, subjects may move during a scan, and so later images may be acquired over shorter windows (for example, 5 minutes each) so that corrections can be made for motion. The time course of radioactivity captured by the series of images may then be used to form "time activity curves" for different regions of interest ("ROIs"), as shown in the example of FIG. 2. Specifically, in the initial stage 200 following tracer injection, signal intensity can increase quickly, largely reflecting tracer influx from plasma into tissue, and can be highly correlated with regional cerebral blood flow rate ("rCBF"). Following a non-equilibrium stage 202 during which the tracer accumulates in target-rich regions, an equilibrium stage 204 is then reached. The time to reach equilibrium can vary depending upon the particular tracer, the region of accumulation, and target load. For example, the equilibrium for florbetapir occurs at about 40-45 minutes, for 11C-PiB at about 45 minutes, and for flutemetamol at about 80 minutes.

In analyzing PET images to determine amyloid burden, kinetic modeling methods are often used. These typically techniques use the entire time activity curve and blood measurements, and solve a set of differential equations characterizing tracer influx and efflux from various tissue compartments. In this manner, blood flow rate, clearance rate, and tracer binding can be quantified. In some simplified models, time activity curve ratios between target regions and regions in which tracer binding is negligible are computed to eliminate the discomfort and logistical issues associated with arterial blood sampling. This produces a Binding Potential ("BP") value that when added to 1 produces a Distribution Volume Ratio ("DVR"), which indicates amyloid burden. The DVR is typically compared to a threshold value to establish whether a patient is considered to be positive or negative for amyloid plaque.

Some kinetic models have demonstrated better robustness, noise, and bias characteristics compared to others. Also, some models have been shown to be better suited for dissociating PET signal contributions from blood flow and rate of tracer clearance, compared to the standardized uptake value ratio ("SUVR") method, for instance, as described below. However, complete activity information from the time of injection until equilibrium is often needed, requiring appreciable patient scanning. Attempts to apply kinetic modeling using activity curves where equilibrium has not been reached, for instance in the first 20 minutes of a florbetapir scan, have resulted in failure.

Since it is often not practical to keep a patient in the scanner for imaging lasting 45 to 90 minutes, alternate amyloid burden measures are often used. In SUVR techniques, for instance, amyloid burden is often determined using later images. Typical later images are acquired 50 to 70 minutes post injection for florbetapir, or 80 to 120 minutes post injection for flutemetamol. The SUVR is then computed by dividing the mean signal intensity of a region or volume of interest ("VOI") by the average intensity of a reference region. Typical VOIs used for determining amyloid plaque burden include the frontal cortex or anterior cingulate, while reference regions include the gray cerebellum, where amyloid plaque is not known to accumulate.

By way of example, FIG. 3 shows amyloid PET images highlighting typical VOIs (e.g. the anterior cingulate, posterior cingulate and precuneus) in a first image 300, and a reference region (e.g. gray cerebellum) in the second image 302. To support a diagnosis of AD or inclusion in a clinical trial, computed SUVR values are compared to a threshold to determine whether a patient is positive or negative. In some approaches, a "cortical average" is often calculated using four to six individual VOIs that are highly correlated, such as the frontal, anterior and posterior cingulate, lateral temporal, and parietal regions.

Although high correlation has been shown between SUVR and DVR measurements, with both resulting in important discrimination between AD patients and normal controls, and modest but positive mean rates for amyloid accumulation over time, these have a number of drawbacks. For instance, as described, DVR measurements require long acquisitions, starting immediately post-tracer injection and extending toward tracer equilibrium, to obtain full time activity curves. On the other hand, SUVR measurements do not take into consideration early information, and do not distinguish contributions of blood flow and clearance. Because of this and other factors, SUVRs often overestimate amyloid burden, a bias that increases with later images due to a lack of true equilibrium between plasma and tissue as the tracer clears from plasma. If tracer delivery and clearance were similar within a subject group, this bias would result in a simple scalar difference in empirically generated thresholds for SUVR versus DVR values. However, it is known that different subjects exhibit differences in longitudinal changes in blood flow and/or clearance, complicating analysis.

A study in AD, mild cognitive impairment ("MCI"), and healthy controls using 11C-PiB showed that while longitudinal reductions in late image SUVR values were observed in AD subjects, there was little or no change when dynamic modeling was used. The decline in SUVR values in AD subjects paralleled a decrease in the uptake rate of the tracer from blood into brain: detected by the k1' rate constant derived from kinetic modeling but not from SUVR calculations. Thus, apparent decreases in SUVR values may be driven by reductions in cerebral blood flow in AD, which is a consideration for longitudinal studies following disease progression. Despite these limitations of the SUVR approach for the purpose of detecting whether a patient is "amyloid positive," and for the purpose of measuring longitudinal change in large multi-site populations, the SUVR method remains the most broadly applied technique.

Therefore, given the above, there is a need for improved systems and methods for determining the presence and progression of a brain condition of a subject using PET images.

SUMMARY OF THE DISCLOSURE

The present disclosure overcomes the drawbacks of aforementioned technologies by providing systems and methods for accurately identifying the brain condition of a subject. Specifically, the present disclosure describes an approach for utilizing Positron Emission Tomography ("PET") imaging information to detect and differentiate various brain conditions. Using a classifier constructed from single or combinations of multiple time frames of image data, various information such as the amount of amyloid plaque, tau, or other entities in the brain may be obtained and used to determine a brain condition of a subject, such as dementia types and degrees of progression.

In some aspects, early PET information obtained following administration of one or more radioactive tracers may be utilized to generate a classifier. For instance, measurement of tracer uptake characteristics indicative of neurodegeneration or dementia may be obtained within the initial minutes following radiotracer injection. In addition, measurements of tracer uptake and binding characteristics indicative of amyloid (or other target) burden may also be obtained within a relatively brief time following radiotracer injection.

In accordance with one aspect of the disclosure, a method for constructing a classifier for identifying a brain condition of a subject is provided. The method includes receiving image data obtained from a plurality of subjects, wherein the image data is acquired during an acquisition period following administration of at least one radioactive tracer. The method also includes defining a plurality of brain condition classes using the image data associated with one or more time frames during the acquisition period, and processing the image data to generate signatures corresponding to each of the plurality brain condition classes. The method further includes constructing a classifier using the signatures.

In accordance with another aspect of the disclosure, a method for identifying a brain condition of a subject is provided. The method includes receiving image data associated with a subject's brain, and applying a classifier to the image data to determine a degree to which the patient expresses one or more disease states. The method also includes determining a brain condition of the patient using the determined degree, and generating a report indicative of the brain condition of the patient.

In accordance with yet another aspect of the disclosure, a system for identifying a brain condition of a subject is provided. The system includes an input configured to receive image data associated with a subject's brain, and a processor configured to construct a classifier comprising signatures of different disease states using images acquired during an acquisition period following administration of at least one radioactive tracer, and apply the classifier to the image data to determine a degree to which the subject expresses the disease states. The processor is also configured to determine a brain condition of the subject using the determined degree, and generate a report indicative of the brain condition of the subject. The system also includes an output configured to provide the report to a user.

The foregoing and other advantages of the invention will appear from the following description.

BRIEF DESCRIPTION OF THE DRAWINGS

The present disclosure will hereafter be described with reference to the accompanying drawings, wherein like reference numerals denote like elements.

FIG. 5 is shows example brain disease classes, in accordance with aspects of the present disclosure;

DETAILED DESCRIPTION

Figure 1A:
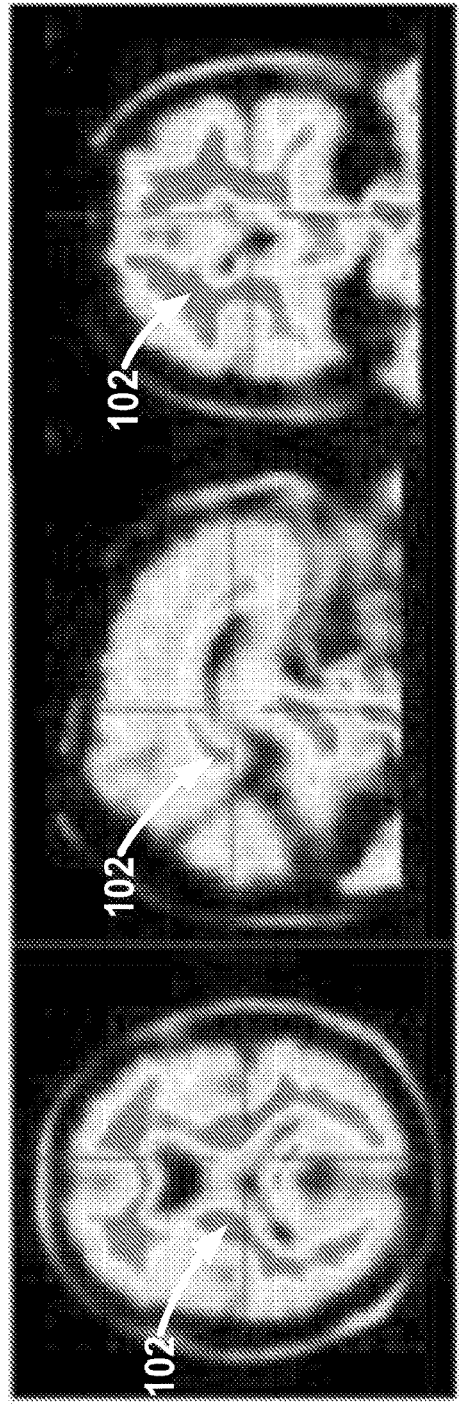
FIG. 1A shows example positron emission tomography ("PET") images for a subject exhibiting a negative amyloid burden.
Figure 1B:
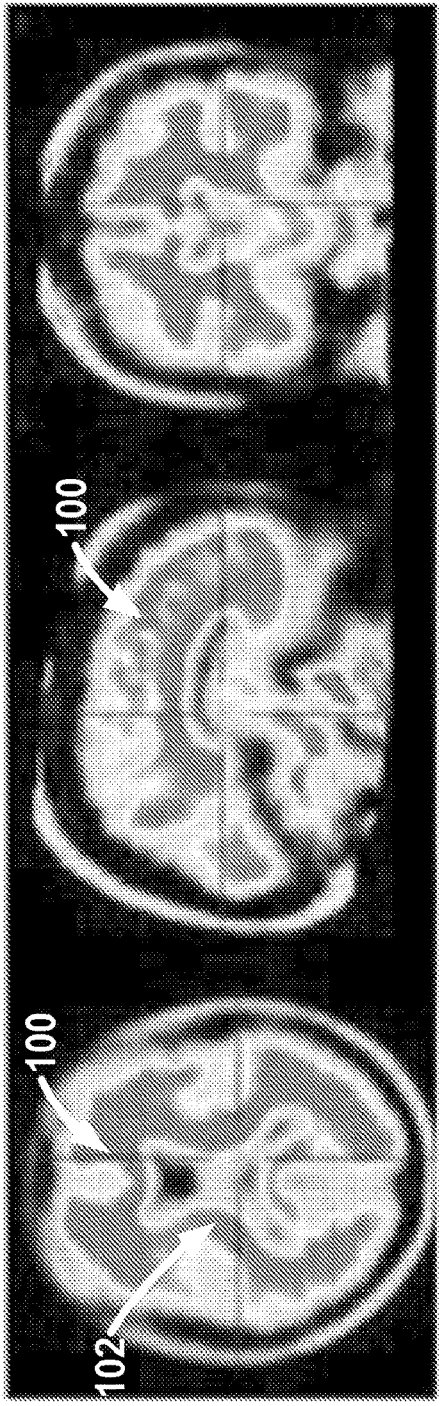
FIG. 1B shows example PET images for a subject exhibiting a positive amyloid burden.

The present disclosure provides systems and methods for accurately identifying brain conditions of subjects, using positron emission tomography ("PET") imaging information, by generating and using classifiers to detect and differentiate different brain disease states, such as dementia and dementia progression states. In particular, one novel aspect of the present disclosure pertains to the use of the discrete time frames as inputs to develop a classifier for detection of a target burden, without requiring the continuum of temporal information that is necessary in traditional kinetic modeling. Making use of different time frames, or combinations of different time frames, as discrete image classes, a classifier generated therefrom can then dissociate time-varying signal patterns associated with a target binding from one or more signal patterns that vary in association with non-specific binding, perfusion, or other properties. As such, the classifier is able to determine the target burden even when an administered radiotracer equilibrium has not yet been reached, Another novel aspect of the present disclosure pertains to the application of the classifier to independent test scans, in which one or more of the discrete frames may be used by the classifier and compared to the patterns that were generated using the discrete timeframe information. Features and advantages afforded by the present disclosure will be apparent in the following description.

In some aspects, a classifier including various disease state signatures may be generated based on imaging data, and information derived therefrom, as will be described. Specifically, image patterns associated with various disease states may be constructed using PET imaging data from one or more time frames associated with the acquisition period following radioactive tracer administration. As mentioned, in some aspects, image patterns may be constructed using data from specific time frames, as well as mathematical combination of multiple time frames. Specifically, the ability to quantify amyloid burden shortly after radiotracer injection is highly desirable. Therefore, in some implementations, early time frames may be utilized to assess amyloid burden. Images acquired from a subject may then be compared to such image patterns to determine the particular disease state(s) exhibited by the subject. In this manner, a variety of medical information about the subject can be produced, such as whether the subject is amyloid positive or negative, or a relative quantity of amyloid plaque that is present in the subject's brain. Using such information, a dementia type, such as Alzheimer's Disease ("AD"), or a degree of dementia progression may be determined. In some aspects, such determination may be correlated with a future cognitive and functional state or condition.

As described in the present disclosure, "early" time frames refer to time frames assembled using imaging data, and other data acquired shortly following radiotracer administration, but prior to the radiotracer(s) having reached equilibrium or pseudo-equilibrium. For example, early time frames may be obtained up to approximately 20 minutes following radiotracer administration, or somewhat longer depending upon the occurrence of the equilibrium or pseudo-equilibrium. On the other hand, "late" time frames refer to time frames assembled using data acquired after the administered radiotracer has reached equilibrium or pseudo-equilibrium. For example, late time frames may be obtained approximately 40 to 80 minutes following radiotracer administration, depending upon the radiotracer utilized.

As mentioned, in some implementations, early time frames may be advantageously utilized to assess amyloid burden. As such, the acquisition period may be relatively short, that is, approximately 20 minutes or more. Use of early time frames is in contrast to traditional methods, which require long scans to quantify amyloid burden. For instance, previous standardized uptake value ratio ("SUVR") methods or kinetic modeling approaches involve lengthy data acquisitions or appreciable wait times, typically 50 minutes or more. In addition to providing information about function or neuro-degeneration, early time frames can provide further advantages in that they take blood flow into account within a relatively short duration scan. In some implementations, however, the acquisition period may be longer, for example, lasting approximately 30-40 minutes, or longer. As such, late time frames may also be utilized to assess amyloid burden.

Figure 2:
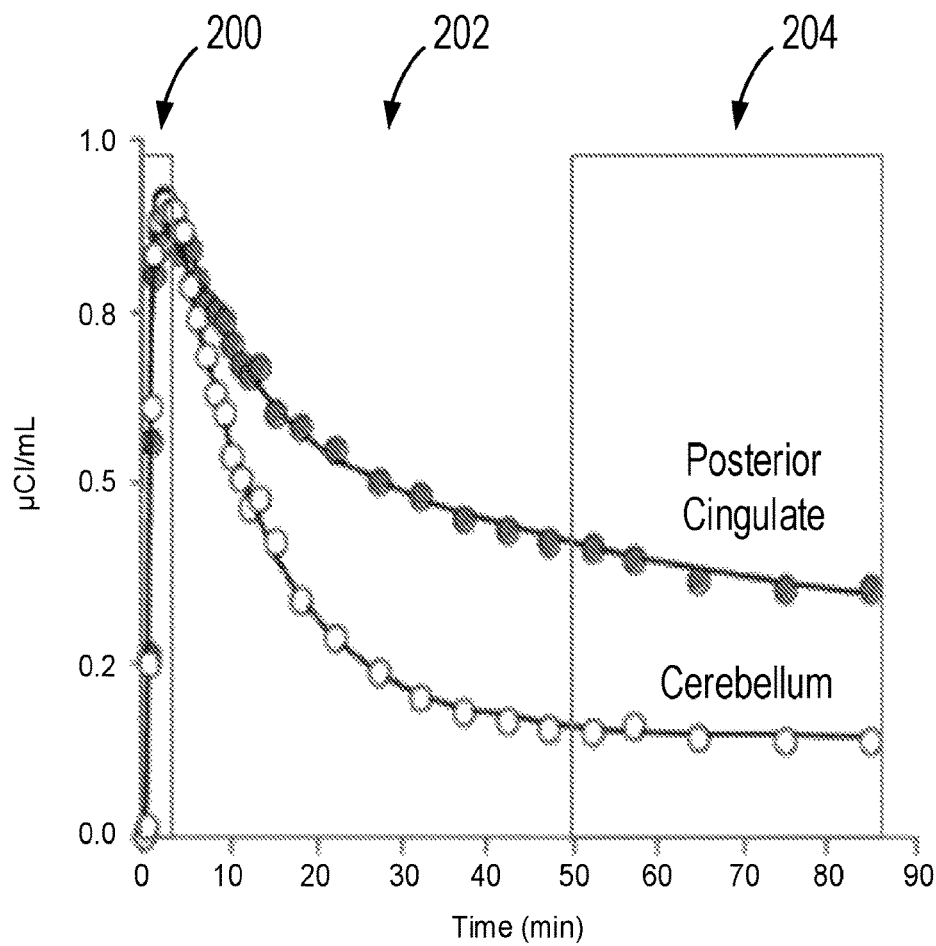
FIG. 2 is a graphical example showing time activity curves for different brain tissues.
Figure 3:
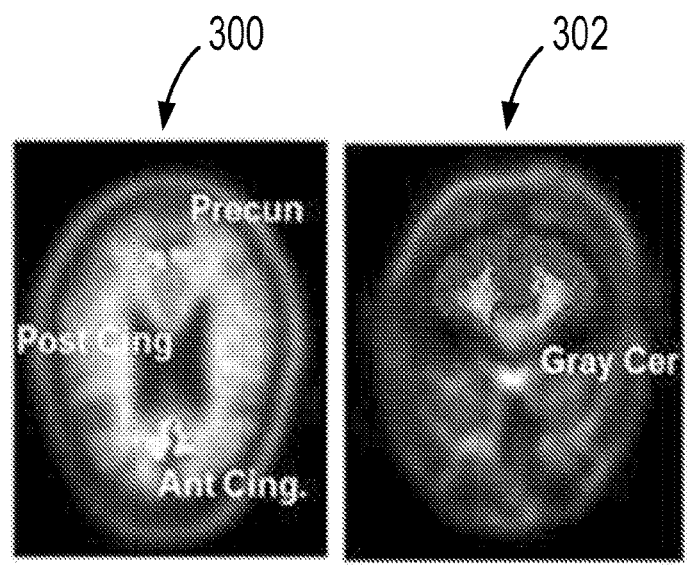
FIG. 3 are images depicting regions of interest utilized for computing standardized uptake value ratios ("SUVRs") in the brain.

Therefore, in some aspects, the acquisition period may extend over an initial stage of a time activity curve, as described with reference to the example of FIG. 2. In other aspects, the acquisition period may extend over the initial stage and a portion of a non-equilibrium stage. In yet other aspects, the acquisition period may extend over the initial stage, the non-equilibrium stage, and a portion of equilibrium stage. As may be appreciated, the duration of the acquisition period can vary depending upon the particular tracer, region of accumulation, and target load. In addition, the time window or duration of each time frame of image data may vary between a few seconds to a few minutes, and may depend upon the elapsed time from radiotracer administration.

As will be appreciated from descriptions below, the advances provided by the present disclosure are applicable not only to imaging of amyloid plaque in the brain using PET, but also to other targets in the brain involving other radiotracers including, but not limited to radiotracers for tau, neurotransmitters, neurotransmitter transporters, inflammation, and alpha synuclein, as well the extraction of information regarding brain function in addition to amyloid burden within a single scan. In addition, systems and methods of the present disclosure can be applied to non-brain measurements, as well as utilize various imaging modalities, such as Single Photon Emission Computed Tomography ("SPECT") imaging, and other modalities providing similar information.

Figure 4:
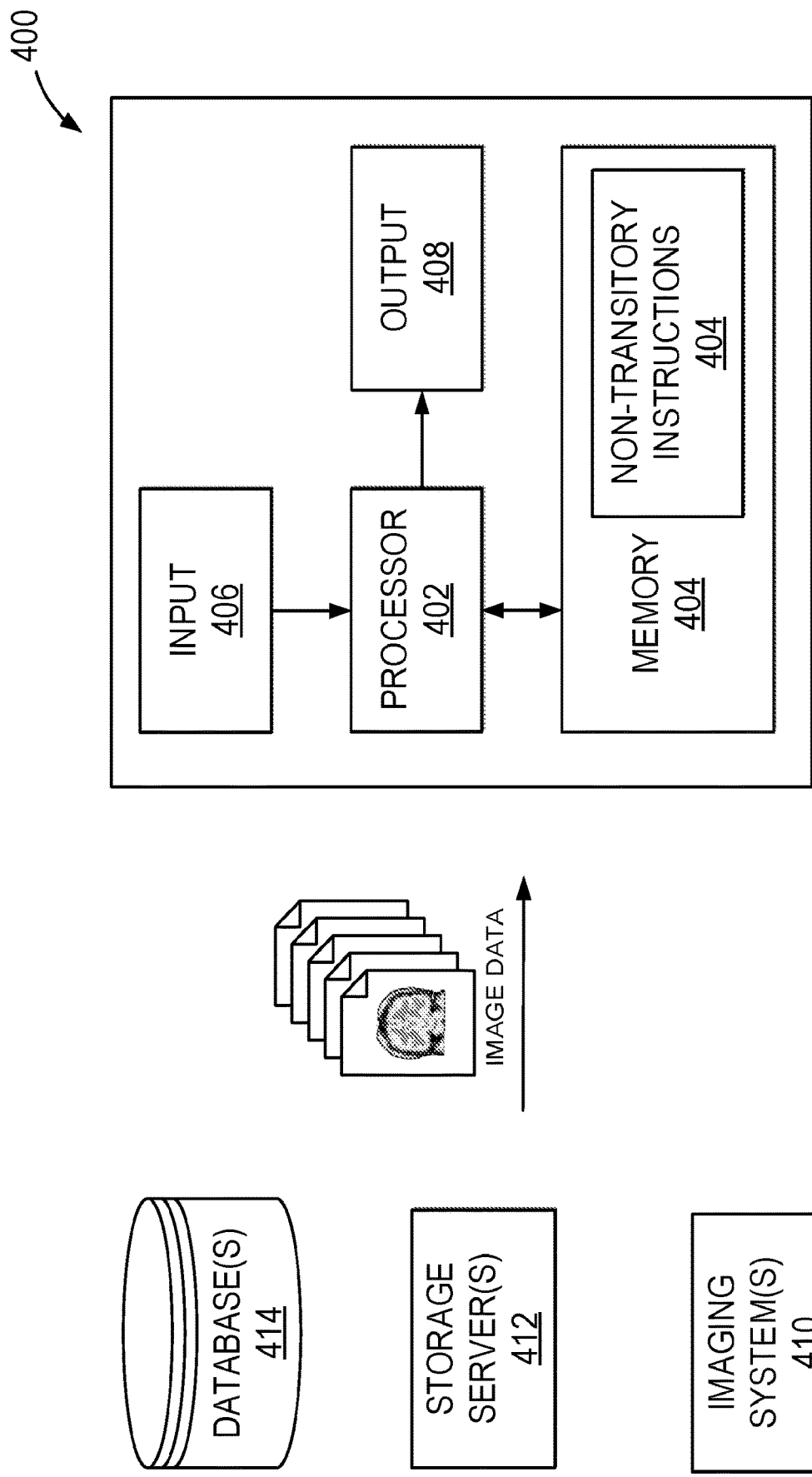
FIG. 4 is a diagram of an example system in accordance with aspects of the present disclosure.

Turning now to FIG. 4, a block diagram of an example system 400, in accordance with aspects of the present disclosure, is shown. In some configurations, the system 400 can include a processor 402, a memory 404, an input 406, an output 408, and may be configured to carry out steps, in accordance with methods described herein, including identifying a brain condition of a subject using image data, and other data.

In general, the system 400 may be any device, apparatus or system configured for carrying out instructions for, and may operate as part of, or in collaboration with, a computer, system, device, machine, mainframe, or server. In this regard, the system 400 may be a system that is designed to integrate with a variety of software and hardware capabilities and functionalities, and may be capable of operating autonomously. In some aspects, the system 400 may be portable, such as a cellular phone, mobile device, tablet, or other portable device or apparatus.

The input 406 may be configured to receive a variety of information or selections from a user in the form of different input elements, such as a mouse, keyboard, touchpad, touch screen, buttons, and the like. As shown in FIG. 4, the system 400 may also be configured to receive information directly from an imaging system 410, storage server 412, or database 414, by way of wired or wireless connection, as well as via flash-drive, compact disc, or other computer-readable medium, via input 406. In some aspects, the processor 402 may receive processed or unprocessed reference data and information associated with a plurality subjects. By way of example, reference data may be accessed from a variety of sources including Alzheimer's Disease Neuroimaging Initiative ("ADNI"), ADNI DoD Traumatic Brain Injury Database, National Institutes of Neurobiological Disorders and Stroke, Parkinson's Progression Markers Initiative ("PPMI"), Dominantly Inherited Alzheimer's Study ("DIAN"), Adult Child Alzheimer's Study (Washington University), Memory and Aging Center Database (University of California San Francisco) and so forth.

Exemplary received or accessed information may include image data, such as PET, SPECT, as well as Computed Tomography ("CT") data, Magnetic Resonance Imaging ("MRI") data, and so forth. Other non-limiting examples include data associated with performance or behavior, cognitive and functional test scores, genotype, Cerebrospinal Fluid ("CSF") levels, e.g. Abeta42, Total tau, ptau alpha-synuclein, blood based biomarkers, other test scores, e.g. sense of smell, amyloid content in eye, and so forth, as well as subject characteristics, demographic, medical histories, and so forth.

In addition to being configured to carry out steps for operating the system 400 using instructions stored in the memory 404, the processor 402 or pre-processing unit (not shown in FIG. 4) may be configured to perform a number of pre-processing steps on data or information associated with one or more subjects. In particular, in accordance with aspects of the present disclosure, image data associated with early time frames are utilized by the processor 402. For instance, PET image data acquired over an acquisition period of approximately 20 minutes, for example, following administration of one or more radioactive tracers may be assembled into one or more time frames from which one or more images may be reconstructed. By way of example, a time frame may be assembled to include image data acquired within the first 6 minutes following radioactive tracer administration. In another example, a time frame may be assembled to include image data associated with the first through the sixth minute of acquisition. It may be appreciated that time frames that include data acquired over any duration may be possible, and may depend upon the specific radioactive tracer being utilized. In some aspects, time frames corresponding to one or more subjects may be averaged, summed, integrated, or otherwise combined to maximize the usefulness of signal information associated with those time frames.

Pre-processing steps carried out by the processor 402 can also include corrections for image orientation, inter-frame motion, as well as spatial normalization to a common brain template. In some aspects, the processor 402 may perform a smoothing to achieve uniform resolution and/or improve overlap when using image data from various scanner types. Also, the processor 402 may perform z-scoring intensity normalization, or other forms of intensity normalization, either to a whole brain, or to a common reference region. For instance, this may include dividing all voxels in an image by a mean value in the reference region. Alternatively, scans may be z-scored to their mean value. Pre-processing may or may not make use of all of these steps, and need not be carried out in their entirety or in the specific order outlined above.

In some aspects, the processor 402 may be configured to process image, and other data, to construct a classifier including signatures corresponding to various brain conditions. Such signatures may include specific target binding, such as amyloid plaque, glucose metabolism, and other signatures associated with different regions of interest ("ROIs") in the brain and associated with various disease states.

In constructing the classifier, the processor 402 may be configured to define a plurality of brain condition classes using image data associated with one or more time frames. The processor 402 may then be configured to apply the classifier the image data, such as amyloid PET data, obtained from a subject identify a brain condition of the subject. For instance, in the case of a dementia differentiation classifier, classes may be defined based upon clinical diagnosis, amyloid status, and other factors that may include age-matching. In one implementation, these may include a Normal amyloid negative class, a Mild Cognitive Impairment ("MCI") amyloid positive class, an AD amyloid positive class, Fronto-temporal Dementia (frontal variant) class, a Semantic Dementia class, and a Lewy Body disease class. In other implementations, other diseases or different disorders may be included. In the case of an Alzheimer's disease progression classifier, classes may be defined based upon clinical diagnosis, amyloid status, and other factors that may include age-matching or range constraints, gender, ApoE e4 carrier status, or other attributes. In one implementation, classes include Normal amyloid negative, Normal with Subjective Memory Complaint amyloid negative, Normal and Subjective Memory Complaint amyloid positive, MCI amyloid positive, and AD amyloid positive. In other implementations, MCI classes may be further sub-divided according to "Early" or "Late" MCI and according to the time from initial MCI diagnosis to conversion to AD, based upon retrospective data, for instance.

Figure 6:
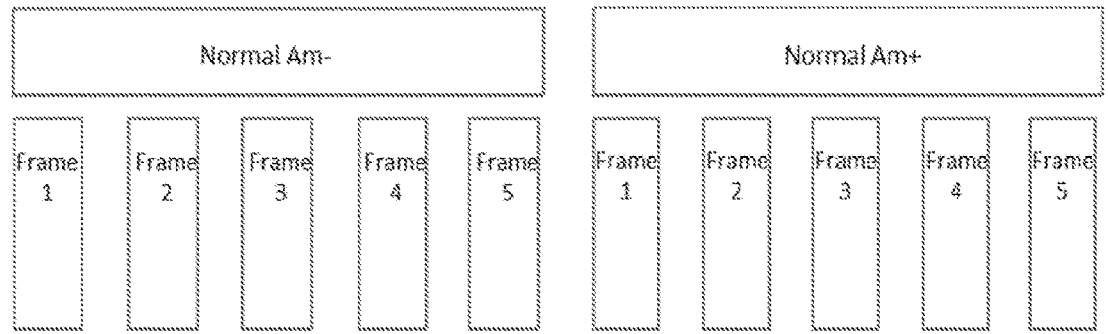
FIG. 6 shows another example of brain disease classes, in accordance with aspects of the present disclosure.

These and other examples of brain condition classes are shown in FIG. 5. In addition, in accordance with aspects of the present disclosure, brain condition classes may utilize image data associated with discrete time frames. Other example brain condition classes includes one or more of an Alzheimer's Disease class, a fronto-temporal dementia class, a Lewy Body Disease class, a vascular dementia class, a depression class, an amyloid class, a normal class, a cognitive impairment class, and so on, as well as subclasses thereof. For example, as shown in FIG. 6, brain condition classes for Normal Amyloid negative and Normal amyloid positive groups each include subclasses formed using discrete time frame image data. In some aspects, these subclasses may either be configured in classifier training as separate classes, with no relationship information provided to the classifier but the relationship known to the developer for the purpose of interpreting and making use of the classifier output, or else with relationships identified for classifier training.

Referring again to FIG. 4, in constructing the classifier using defined brain condition classes, the processor 402 may then perform a Principal Component Analysis ("PCA") on the image data. Mathematical combinations of PCs may then be determined through Canonical Variate Analysis ("CVA"), a form of Linear Discriminant Analysis. An optimal number of PCs may be selected based upon metrics of reproducibility and/or prediction. In this implementation, reproducibility and prediction may be determined through the comparison of a large number, for example 50, of iterative random split halves of a given data set. Specifically, one half can serve as a training set and the other half as a test set. Reproducibility may be determined using a mean correlation value between training and test sets, while prediction would involve the mean classification accuracy of the test sets.

In this technique, the number of canonical variates ("CV") may be set to be equal to number of training classes minus 1. As such each CV would be associated with an eigenimage, namely a pattern of intensities forming a three-dimensional image. All CVs or a subset may be relevant for use with independent test data, since one or more CVs may account for nearly all of the variance across the data set. Once CVs are selected, an independent test scan can be compared to the eigenimage by multiplying the intensities of the voxels within the test scan by their corresponding intensities within the eigenimage, and summing them, or by otherwise mathematically comparing the independent test scan to the eigenimages.

Other approaches may be applied by the processor 402. For example, Support Vector Machines ("SVM"), Relevance Vector Machines ("RVM"), Partial Least Squares ("PLS"), or nonlinear algorithms (e.g. Quadratic) may be applied in lieu of CVA to develop the classifier. In addition, variations regarding the way in which the image is compared to each eigenimage may apply, through the use of thresholding, subregion comparisons, or other mathematical formulae. Priors, or weighting, may be applied that influence the classification decision.

In addition, a non-voxel based classifier approach can be applied. For example, the images can be measured using a set of pre-defined or empirically defined regions of interest, and the mean or another representative value for each region used as the image set (i.e. the set of values) for each training and tests scan. The CV patterns (or if not CVA, the component patterns, e.g. LVA in the case of PLS) are then mathematical combinations of these discrete values rather than image patterns.

The processor 402 may then apply a constructed classifier to image data acquired from a subject to determine a degree to which the subject expresses one or more disease states in order to identify a brain condition of a subject. In addition, the processor 402 may determine an amyloid burden of a subject by applying the constructed classifier to image data obtained from a subject, and particularly to early time frame image data, as will be described, in contrast to previous SUVR techniques or other amyloid burden measurement types.

In some implementations, the processor 402 may utilize the determined degree to separate image data obtained from the patient in order to disassociate contributions from individual disease states. Specifically, the processor 402 may produce datasets corresponding to each expressed disease state. In this manner, the produced datasets may be used by the processor 402 to identify and track individual disease states over time, as well as correlate individual disease state with clinical outcomes. In some aspects, the processor 402 may generate one or more images by matching image data from an independent scan to eigenimages of a provided or constructed classifier, generating a visual representation that can provide additional information or clarity regarding specific disease states of the subject.

The processor 402 may then generate a report, in any form, and provide it via output 408. In some aspects, the report may include information indicative of an identified brain condition of the patient. For example, the report may indicate whether analyzed subject is amyloid positive or amyloid negative, is suffering from a particular disease or dementia, or a particular degree of disease progression. In some aspects, the report may provide information regarding a determined amyloid burden. In addition, the report may indicate one or more signatures, images, or image patterns indicative of one or more disease states.

Figure 7:
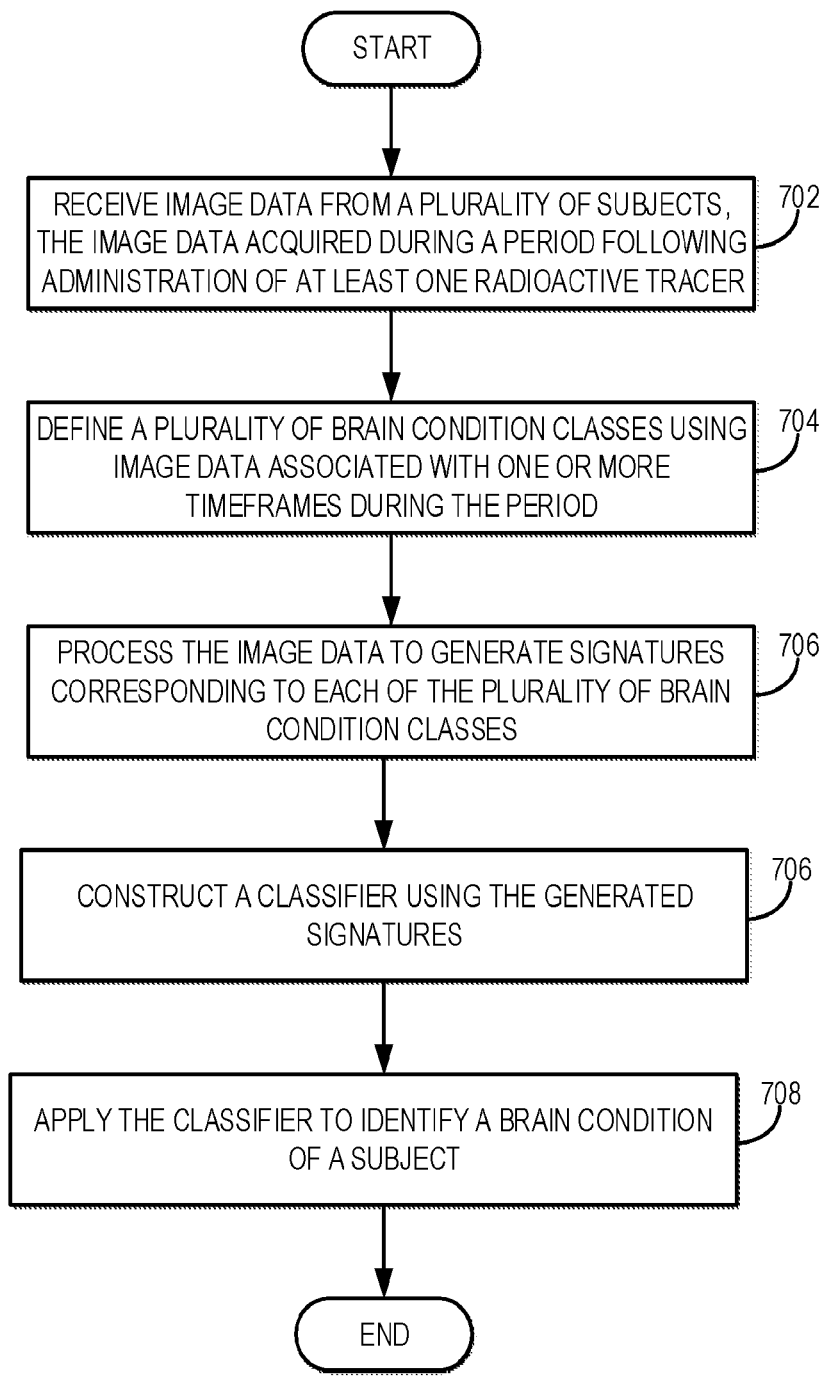
FIG. 7 is a flowchart setting forth the steps of a process in accordance with aspects of the present disclosure.

Referring now to FIG. 7, steps of a process for generating a classifier, in accordance with aspects of the present disclosure, are shown. The steps may be carried out, either entirely or in part, using a system, for example, as described with reference to FIG. 4, or other suitable system. The process may begin at process block 702 whereby datasets including image data associated with a plurality of subjects suffering or at risk from a variety of disease states, are received. For example, subjects may be suffering from Down Syndrome ("DS"), Alzheimer's Disease ("AD"), Parkinson's Disease ("PD"), Dementia, Lewy Body Disease, Traumatic Brain Injury ("TBI"), cognitive impairment, and so forth. In some implementations, the image data received at process block 702 may include PET data. In addition, the image data may be associated with, but not limited to, early time frames following radiotracer administration. For instance, early time frames can include image data acquired within the first 20 minutes post-injection, although data associated with other time frames may also be utilized.

A plurality of brain condition classes may then be defined, as indicated by process block 704. As described, brain condition classes may include one or more Alzheimer's Disease classes, fronto-temporal dementia classes, a Lewy Body Disease classes, vascular dementia classes, depression classes, amyloid classes, normal classes, cognitive impairment classes, and so on, as well as subclasses thereof, for instance in accordance with different time frames following radiotracer administration.

The received datasets may then be used to generate signatures corresponding to each of the plurality brain condition classes, and utilized to construct a classifier, as indicated by process blocks 706 and 708. As described, in some aspects, images reconstructed using image data may be pre-processed. This may include mathematically combining respective image data or images associated with different time frames, as well as performing smoothing, spatial and intensity normalization across subject datasets. In some aspects, an overall mean value may be calculated and removed from the datasets. Also, optionally, rather than utilizing image volumes to generate the classifier, image data associated with particular regions of interest, or aggregate values thereof, may be provided through a selective masking process.

In generating the signatures at process block 706, a principal component analysis may be performed using the received images or image data from the plurality of subjects. This includes determining a number of canonical variates, which are combinations of image patterns that account for the variance across each of the defined brain condition classes. The canonical variates may be determined by identifying the combination of uncorrelated patterns that best differentiates the different classes. The result includes a number of image patterns, forming a classifier, across which independent scans may be scored to identify a brain condition or disease of a subject, as indicated by process block 708. The classifier may be provided, in the form of a report, for example via a display. In some aspects, patterns obtained by mathematically comparing independent scans acquired from a subject to respective canonical variate eigenimages may be used to create images for user viewing, aiding in visual assessment of the image. The implication is that a typical 20 minute amyloid scan, or timeframes associated with those 20 minutes, for example, may not be directly interpretable, while one or more images created after matching the scan to the eigenimages of a provided or determined classifier could be interpretable or provide additional information or clarity.

In some aspects, a determined classifier may be optimized, for instance, through multiple iterations of steps described above performed using training data sets that are divided into halves. A first half, for example, can be used as a training set, while a second half may be used as a testing set. A metric of prediction may be generated for each test scan by comparing it to the training canonical variates, classifying or scoring it, and comparing its classification to its known class. A metric for reproducibility may also be determined through the correlation of the test and training scans. The classifier may then be optimized for a certain number of principal components to maximize reproducibility and prediction.

Figure 8:
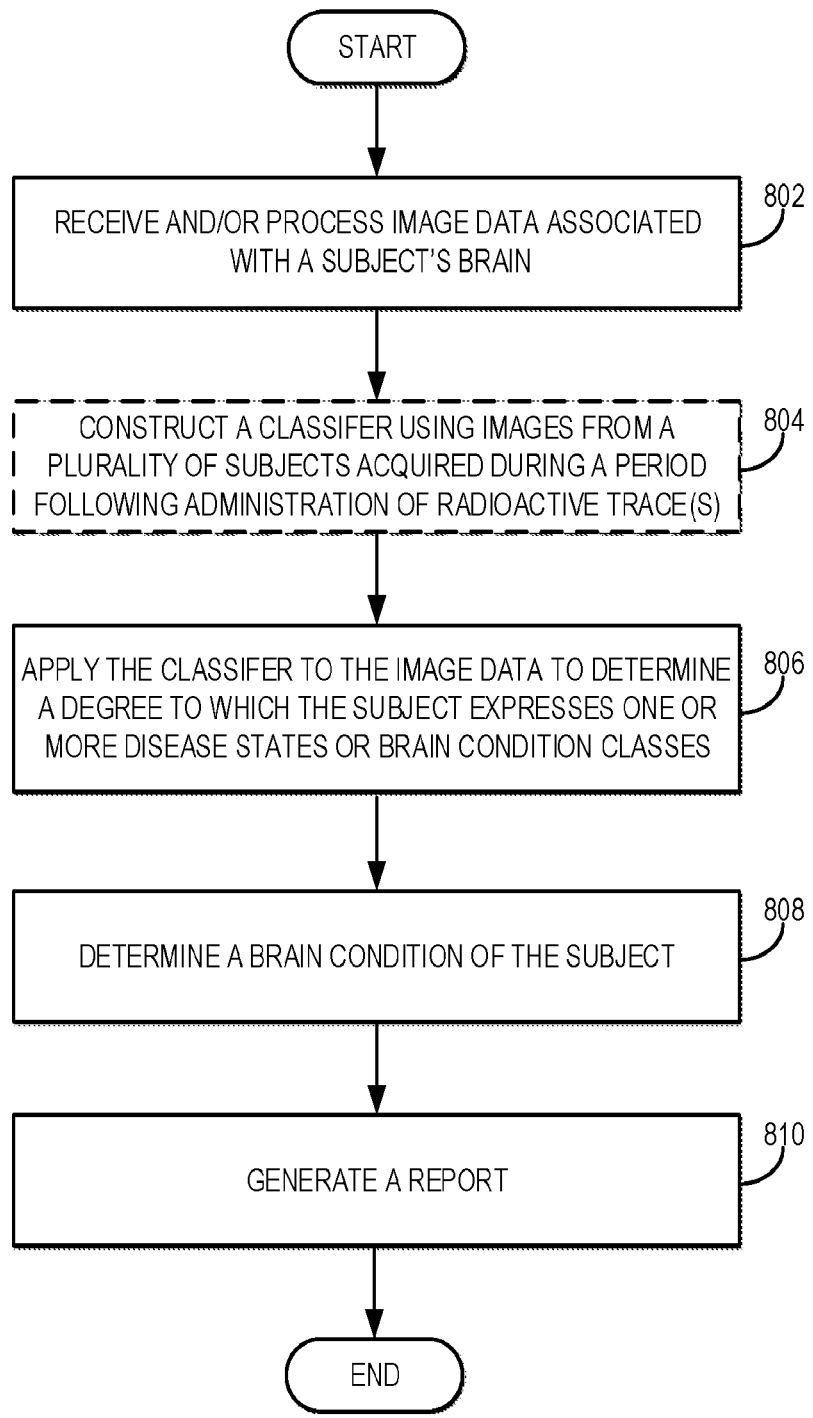
FIG. 8 is another flowchart setting forth the steps of a process in accordance with aspects of the present disclosure.

Referring now to FIG. 8, steps of a process in accordance with aspects of the present disclosure are shown. The steps may be carried out, either entirely or in part, using a system, for example, as described with reference to FIG. 4, or other suitable system. Specifically, the process may begin at process block 802 whereby image data associated with a subject's brain, and as well as data acquired from a subject, is received. The image data may be retrieved from a PET system, a SPECT system, an MRI system, a CT system, or other imaging system, or a storage location, such as a database or storage server. In some aspects, PET image data acquired during an acquisition period following radiotracer administration is received a process block 802. For instance, PET image data associated with one or more time frames acquired over an acquisition period lasting up to approximately 20 minutes, or longer, may be received. However, other subject data may also received at process block 802, including cognitive and functional test scores, genotype, Cerebrospinal Fluid ("CSF") levels, e.g. Abeta42, Total tau, ptau alpha-synuclein, blood based biomarkers, and other test scores, e.g. sense of smell, amyloid content in eye, and so forth.

In some aspects, several pre-processing steps may applied to the received data. For instance, in the case of PET image data, an image reconstruction along with a number of corrections for radioactive decay, scatter, and attenuation may be carried out, as well as corrections for partial volume effects. In order to evaluate and correct for subject motion, PET scans are typically acquired as a series of time frames commonly aligned to one another. In some aspects, such time frames may be combined, for instance by summing or averaging, to generate a single image, or image set for multiple anatomical slices. Alternatively, an image, or image set, may be generated for each time frame. In some aspects, image data, or images reconstructed therefrom, may be normalized or warped to a template space, in accordance with a constructed classifier. Such image data, or images, may also be intensity normalized, for example, by z-scoring to a mean, as described.

Optionally, a classifier may be constructed, as detailed with respect to FIG. 7 and indicated by process block 804. As described, the classifier includes signatures of various disease states, as well as or brain condition classes and sub-classes, for instance associated with various time frames of the image data. Non-limiting examples of disease states and classes include Alzheimer's Disease ("AD") and variants, such as Posterior Cortical Atrophy ("PCA") Logopenic Progressive Aphasia ("LPA"), Early Onset AD, Autosomal Dominant AD, Down's Syndrome ("DS"), Traumatic Brian Injury ("TBI"), Chronic Traumatic Encephalopathy ("CTE"), Post-Traumatic Stress Disorder ("PTSD"), depression, hypothyroidism, Psychosis, Lewy Body Disease, vascular disease, Parkinson's disease ("PD"), Parkinson's disease with dementia ("PDD"), Frontotemporal Dementia ("FTD"), including Frontal variant, Semantic dementia ("SD"), Nonfluent Progressive Aphasia ("NFPA"), Corticobasal Syndrome ("CBS"), Prion Disease, Creutzfeldt-Jakob Disease ("vCJD"), Huntingtons Disease ("HD"), motor neuron disease, Amyotrophic Lateral Sclerosis ("ALS"), Normal Pressure Hydrocephalus ("NPH"), Multiple Sclerosis ("MS"), Alcoholism, Wernicke-Korsakoff syndrome, narcotic syndromes, and other diseases, syndromes or deficiencies, including vitamin related, sleep deprivation deficiencies, as well as various combinations thereof. In accordance with aspects of the disclosure, amyloid burden classes may also be included in the classifier.

A constructed classifier may then be applied at process block 806 to the imaging data, and other data, obtained from the subject, in order to determine a degree to which the patient expresses different classes. In some aspects, applying the classifier may include comparing the imaging data associated with selected regions of interest ("ROIs") to signatures or patterns associated with each of the different disease states to determine the degree to which the patient expresses at least one of the disease state or class. This may include multiplying corresponding intensities in an image acquired from the subject with those from a pattern associated with a brain condition class. Such products may then be summed or otherwise mathematically combined to yield a canonical variate ("CV") score. In some aspects intensities from an entire image may be utilized, while in others, intensities associated with specific regions of interest, such as the left and right brain hemispheres, for instance, may be utilized.

CV scores can then be compared to various threshold values established for different classes, such as Normal Amyloid negative, Normal amyloid positive, or other increasing levels of severity. Based on statistical distance from such thresholds, the image or images analyzed may be assigned to one or more classes. In particular, in the case that multiple CVs are involved, for instance for multiple regions of interest, a linear or non-linear combination of such scores may be compared to a benchmark associated with the different classes. An overall distance may then be determined in order to perform a class assignment. In addition, for classes associated with different discrete time frames, relationships such as slope or shape of a CV score curve may also be evaluated and utilized in classification. An algorithm may be applied to assign the subject image or images, including discrete time frames, to a disease state class or amyloid burden class. In one embodiment, information from early time frames may be used to correct for blood flow changes that may affect amyloid burden measurement in later pre-equilibrium (or later) timeframes.

In this manner, a degree to which the subject expresses one or more disease states or classes may be determined, as indicated by process block 808. In some aspects, the presence and/or progression of the brain condition of the patient may be determined, as well as a future disease state, using the respective datasets or information obtained therefrom. The determined brain condition may then be utilized to identify, for instance, a disease progression, or an effectiveness of an administered medication, and so forth. IN other aspects, an amyloid burden may be determined.

A report is then generated, as indicated by process block 810, and provided to a user via an output, such as a display. In some aspects, the report may indicate a degree to which the patient expresses one or more disease states, the presence and/or progression of the brain condition, a projected clinical outcome, a rate of clinical worsening, an amyloid burden, and so forth. The report may also include a classification confidence or accuracy for classification.

Figure 9A:
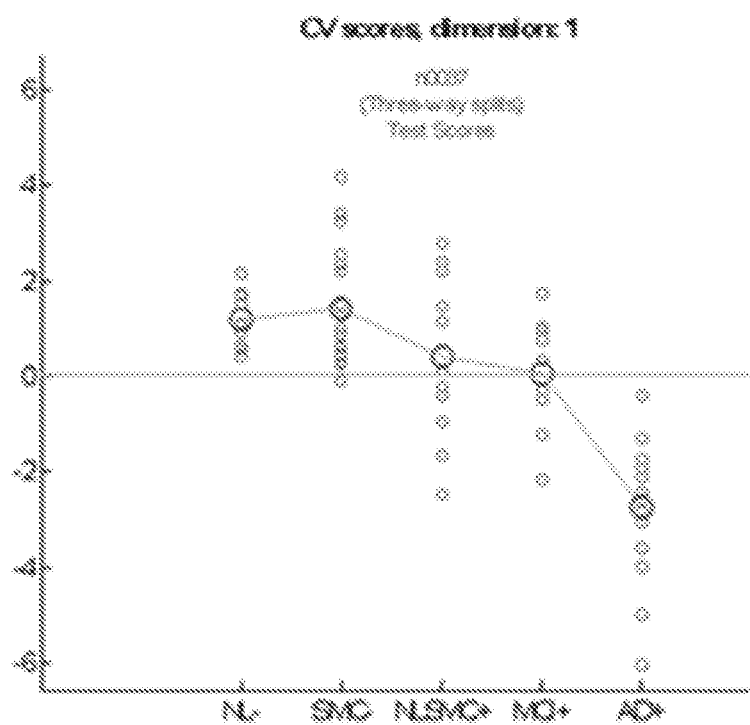
FIG. 9A is a graphical illustration showing canonical variate ("CV") scores for an early frame amyloid classifier, in accordance with aspects of the present disclosure.
Figure 9B:
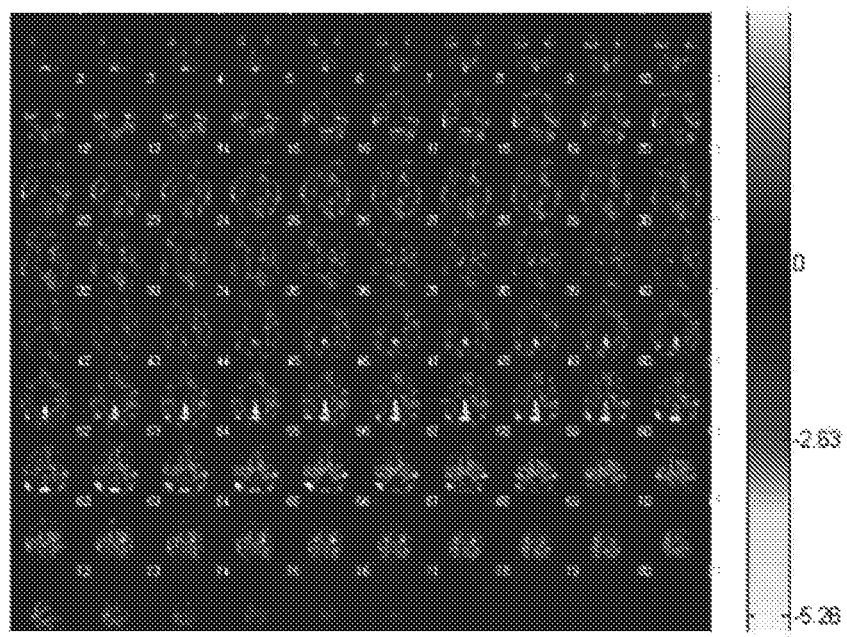
FIG. 9B is a graphical illustration showing image patterns corresponding to FIG. 9A.

By way of example, FIGS. 9A and 9B shows results of one of an implementation using summed time frames from 1 to 6 minutes, voxel-based CVA, and five training classes: Normal (i.e. a clinical diagnosis of Normal) amyloid negative, Subjective Memory Complaint amyloid negative, Normal amyloid positive, Mild Cognitive Impairment (MCI, including Early MCI and Late MCI) amyloid positive, and AD amyloid positive. The results show the Leave-One-Out ("LOO") test values obtained by the classifier, constructed in accordance with the present disclosure. FIG. 9B shows the eigenimage associated with CV1, where it can be noted that the pattern shows decreases in flow or activity in the hippocampus, medial and lateral temporal cortices, posterior cingulate and precuneus, and inferior parietal cortex, while sensorimotor cortex, occipital cortex, a majority of cerebellum, and other regions are relatively preserved. Prefrontal and frontal show some, but lesser relative loss of activity, consistent with FDG PET findings in AD. FIG. 9A shows the eigenplot of LOO CV scores where the score (y-axis) represents the degree to which each subject is expressing the pattern shown in the eigenimage of FIG. 9B. The lower the score, the more similar the pattern (which has been inverted to reflect the downward direction) is the subject relative to those on the opposite end of the y-axis.

Figures 10A, 10B:
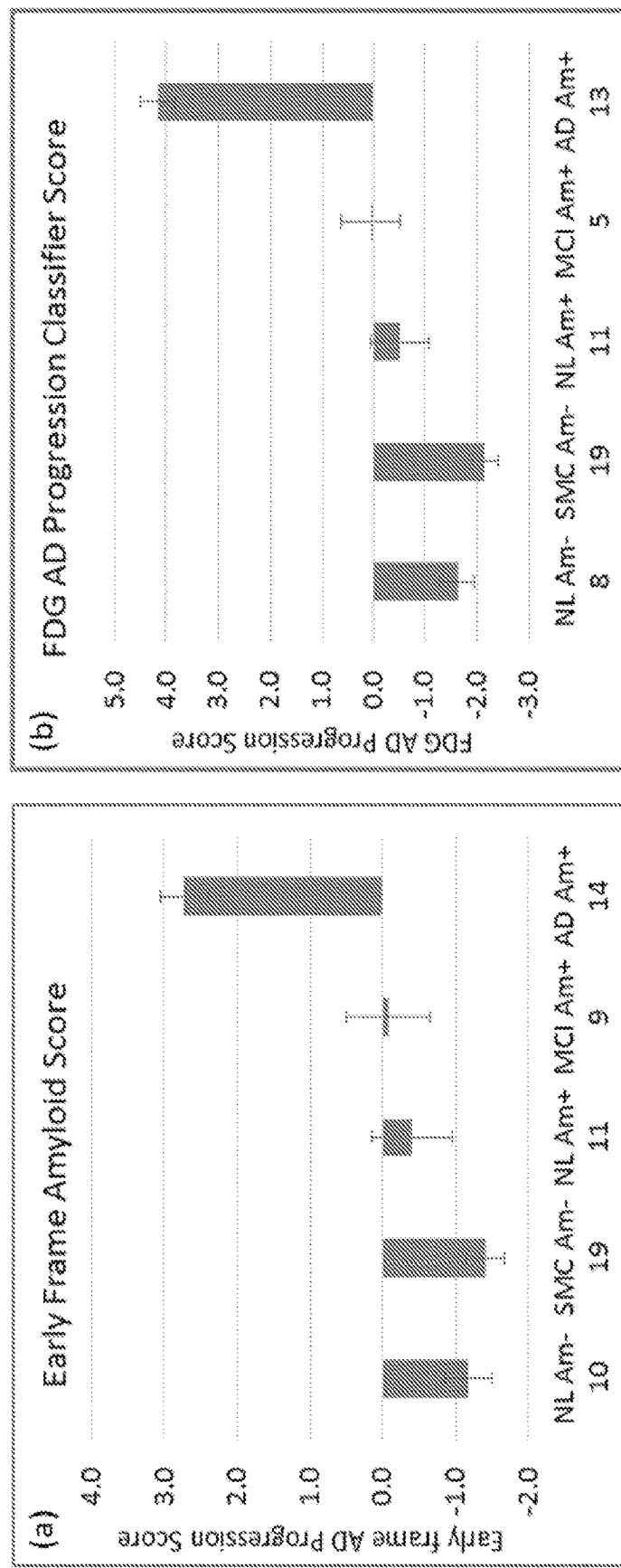
FIG. 10A is a graphical example showing early frame amyloid scores, in accordance with aspects of the present disclosure.
FIG. 10B is another graphical example showing FDG Alzheimer's Disease progression scores.

As another example, FIG. 10A shows the mean LOO values for each group and FIG. 10B shows the mean values obtained by applying a previously developed FDG PET AD progression classifier to the same data where available. The results are highly similar across classes, indicating good correspondence between characterization by the early frame amyloid classifier and characterization by the FDG PET classifier (using FDG PET scans acquired at the same approximate time (within a month) on these subjects), which directly measures glucose metabolism as a reflection of neuronal activity.

As described, in some aspects of the disclosure, a classification of dementia type using dynamic (time course) frames. In this case, rather than summing or otherwise integrating early timeframe, a set of discrete frames may be used, each as its own class. In one implementation, all time frames available (up to a predefined common ending point) may be utilized. For example, 16 frames may have been acquired over a twenty minute period post-radiotracer injection. Thus, all 16 frames per subject, for each of say 5 classes, giving a total of 80 classes (16×5). Such class "hierarchy" may or may not be linked when implemented a machine learning algorithm. For example, all 80 classes may be treated as independent classes without providing the classifier information on which frames are related to which other frames. Alternatively, the 16 frames from each scan may be associated with each other, for a total of five major classes with 16 sub-classes each.

In another implementation, a subset of frames that represent the first few to several minutes (e.g. frames covering minutes 1 through 6) may be used. This yields, for example, 10 frames per diagnostic-amyloid class×5 diagnostic-amyloid classes=50 classes. The number of frames may depend upon the data acquisition protocol (how many seconds or minutes per frame) and the number of minutes included.

In a third implementation, an average or sum certain timeframes in the series may be used, and use others as single discrete frames. In yet a fourth implementation, a second classifier can be built on top of the first classifier that incorporates relationships between the discrete timeframes of each particular grouping.

Given the multiple classes, the feature reduction (e.g. PCA) and machine learning approaches that were described in the non-discrete frame version may be applied. This results in an optimized set of N−1 CVs, where N is the number of classes. In the case of 80 classes, there are 79 CVs. However, only a few of these may account for the majority of variance across classes. These CVs may be used to discriminate between classes. In using the CVs to discriminate between classes, a mathematical combination of one or more CV scores may be used. This could include summation of the CV scores related to a certain time window for a single scan (e.g. a combination of CV's, or integrating across the scores related to a certain time window for a single scan, or calculating the slope or other relationship between the CV scores associated with a single scan.) Because it is known which classes are associated with which time frame and which diagnostic class, sense can be made of the patterns in the mean CV score for each class and hence formulas for final interpretation may be defined accordingly.

Figure 11A:
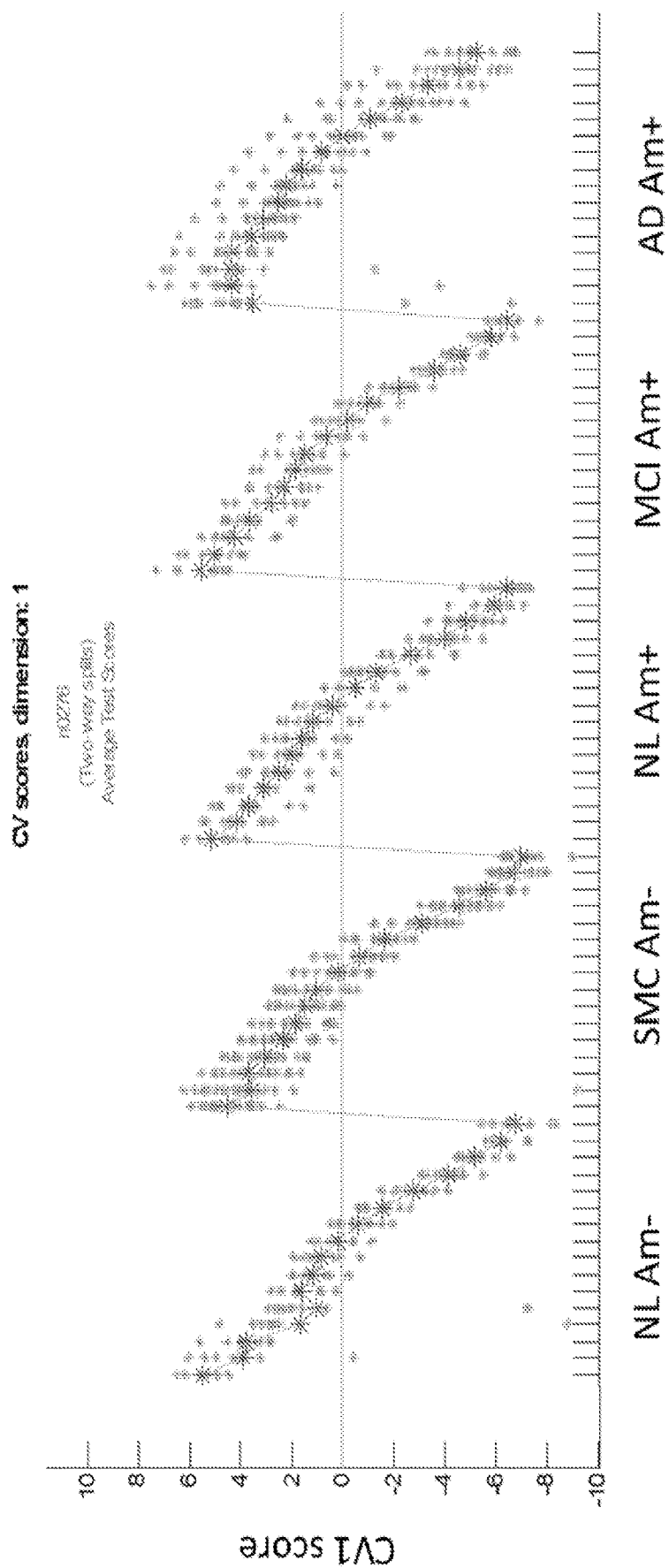
FIG. 11A is a graphical example showing CV scores for an 80 class analysis using discrete frames, in accordance with aspects of the present disclosure.
Figure 11B:
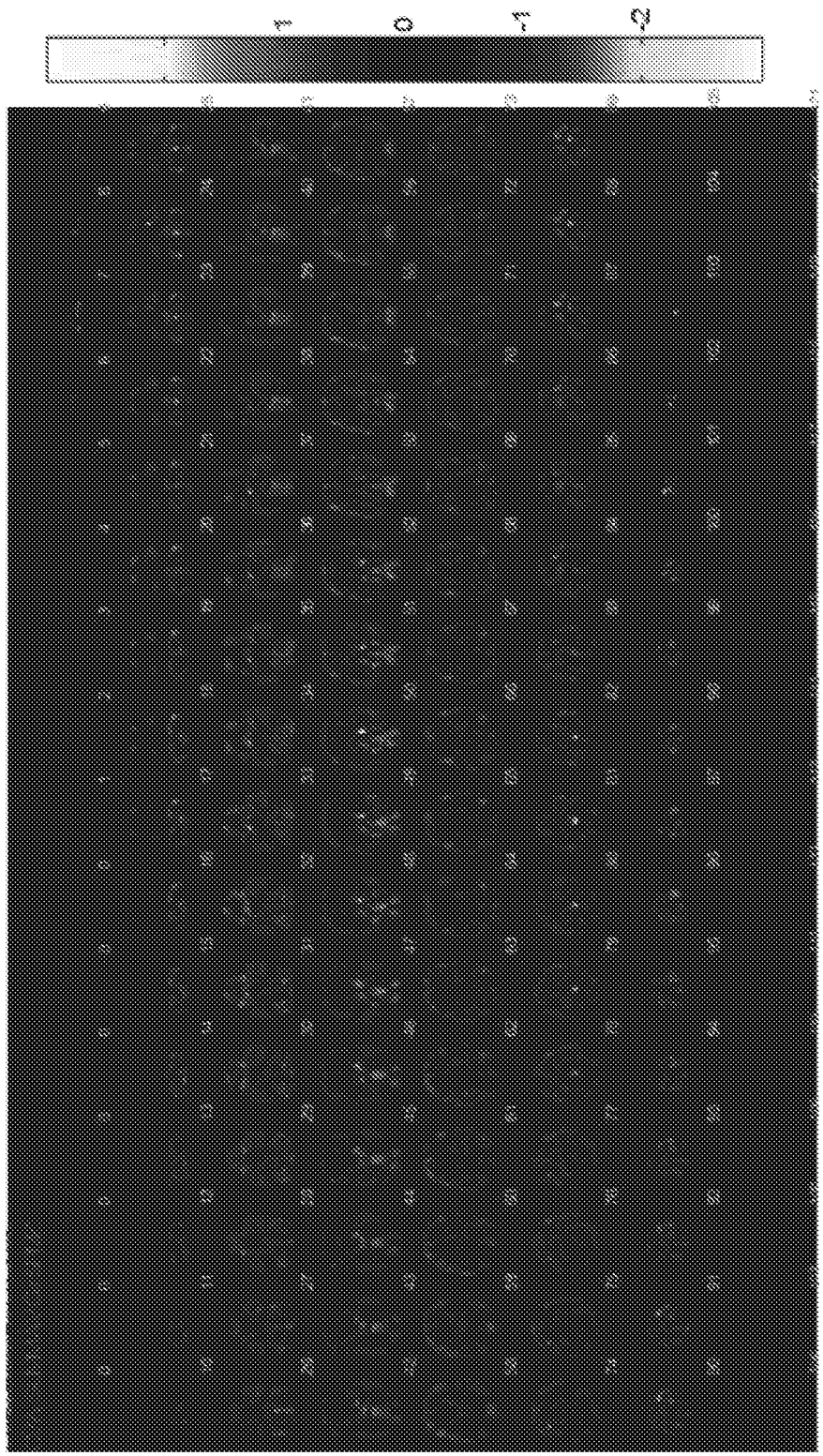
FIG. 11B is a graphical illustration showing image patterns corresponding to FIG. 11A.

By way of example, FIG. 11A below illustrates CV1 score from an "all frame" analysis of a 20 minute florbetapir scan, whereby each of the 16 timeframes for each scan within the five diagnostic-amyloid classes was treated as a separate class. It may be appreciated that the slope for Normal amyloid negative is sharpest, while the slope for AD amyloid positive is the least sharp. Such slope values or integrated regions under CV1 scores for the initial 11 or so frames of an independent test scan could be utilized, also taking into account whether or not they are above or below the zero baseline, to discriminate between these overall diagnostic-amyloid classes. FIG. 11B shows the eigenimage associated with FIG. 11A. The pattern was not inverted for display, and thus those subjects whose scores remained higher in FIG. 11A for a longer period of time were expressing this relative pattern to a greater degree than those whose scores quickly ramp down. This shows that the amyloid positive AD subjects "hold" or express the pattern of relative hypometabolism in AD signature regions, and relative preservation in cerebellum, pons, thalamus, and to some extent white matter, longer than their NL Am-counterparts.

Figure 12A:
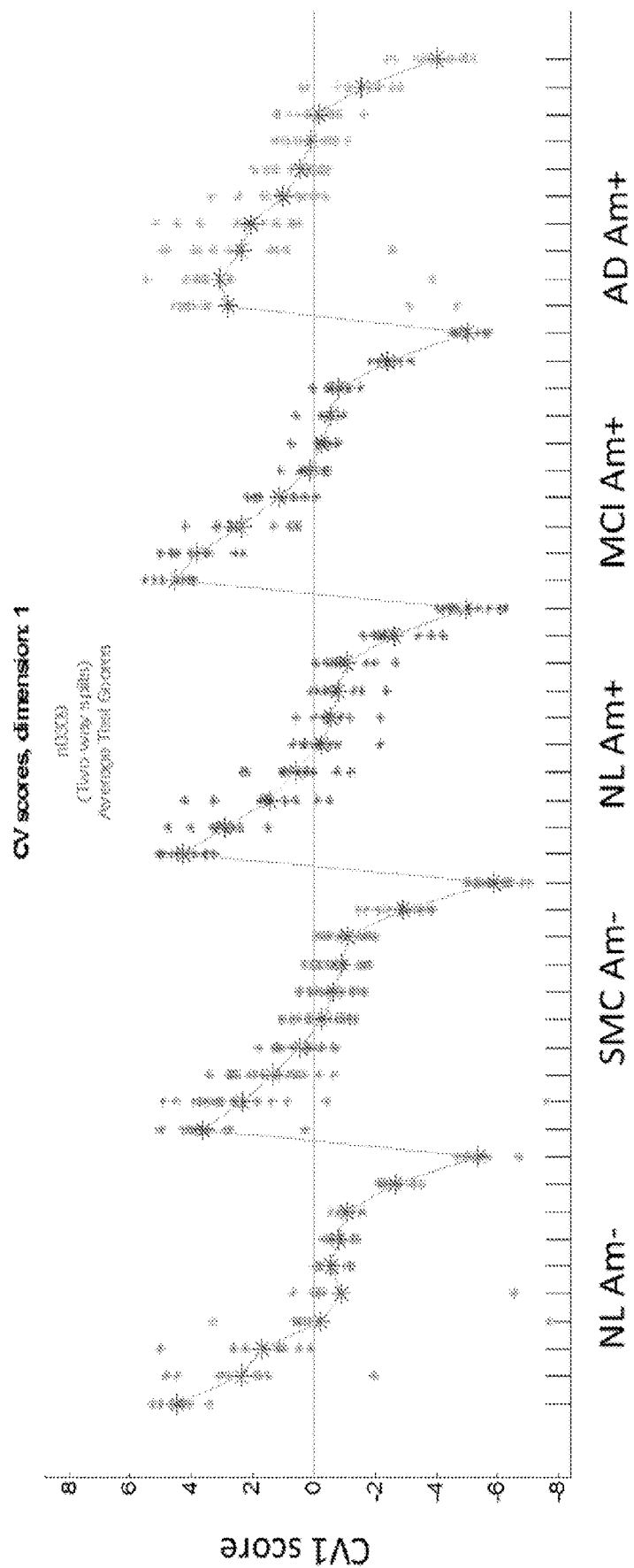
FIG. 12A is a graphical example showing CV scores for a classifier utilizing discrete and combined time frames.
Figure 12B:
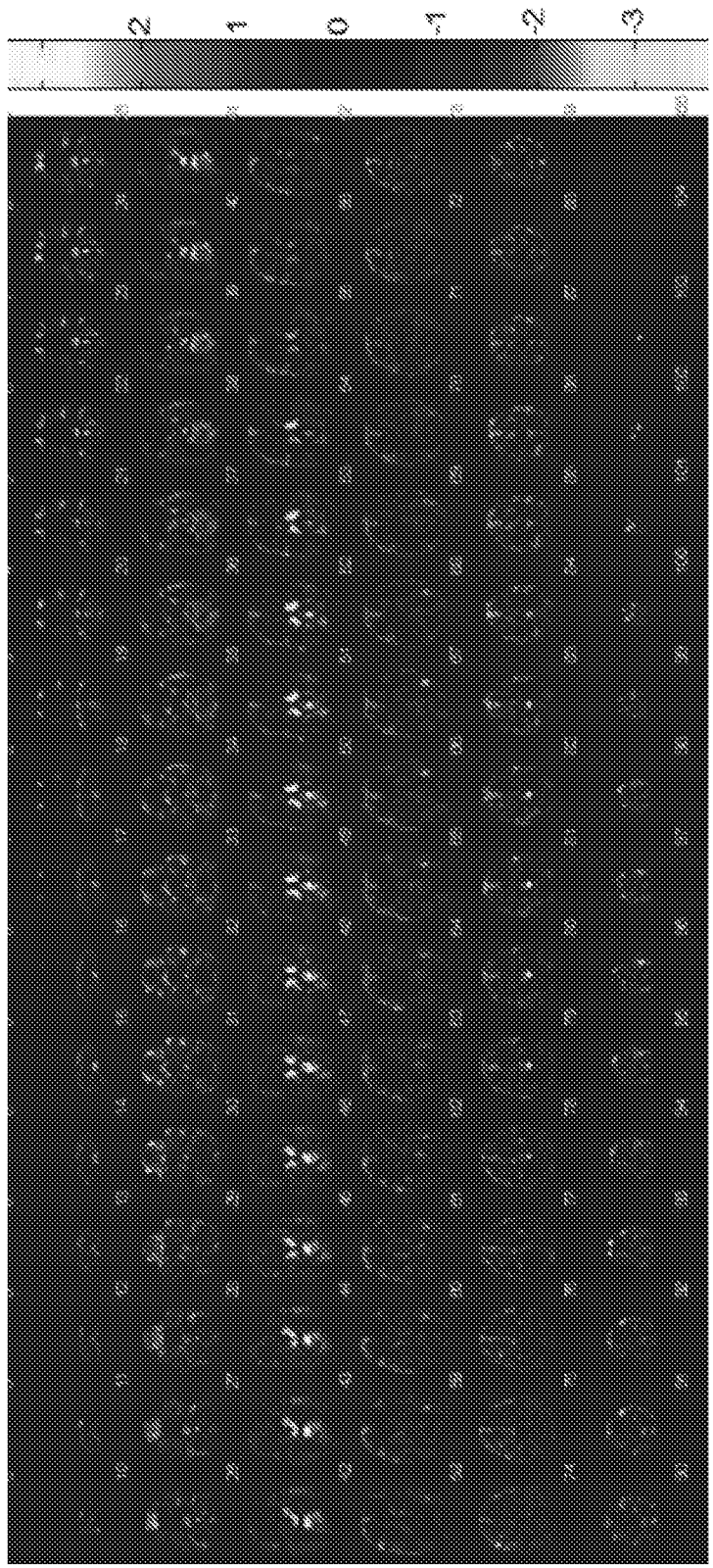
FIG. 12B is a graphical illustration showing image patterns corresponding to FIG. 12A.

FIG. 12A shows CV1 scores from a different "all frame" analysis of a 20 minute florbetapir scan, whereby the initial 8 timeframes for each scan within the five diagnostic-amyloid classes were treated as separate classes, but the middle 4 frames and last 4 frames were each summed to a single point each for a total of 10 frames. It may be seen that the slope for Normal amyloid negative is sharpest, while the slope for AD amyloid positive is least sharp. Note that while for NL Am-, only 3 of the points are above the baseline, with a rapid slope, for AD Am+, 7 points are above baseline, with a much flatter slope. This differs from taking the area under the curve of the original scan, as this area is measured relative to a particular aspect (component pattern) of the scan. As mentioned, the higher the CV score on the y-axis, the more the subject is expressing this pattern in that frame relative to those with lower scores. Note that the blue voxels, or lower blood flow/related signal, feature hippocampal and medial temporal regions, posterior cingulate, and temporoparietal cortices. As observed in summed early frame images, the intensity in the thalamus (low flow) differs from the relative preservation seen in FDG PET scans, but nonetheless there appear to be elements of an AD-progression like pattern. (The pattern may also contain spatial alignment effects that could be reduced through additional image pre-processing.) FIG. 12B shows the eigenimage associated with CV1.

Figure 13A:
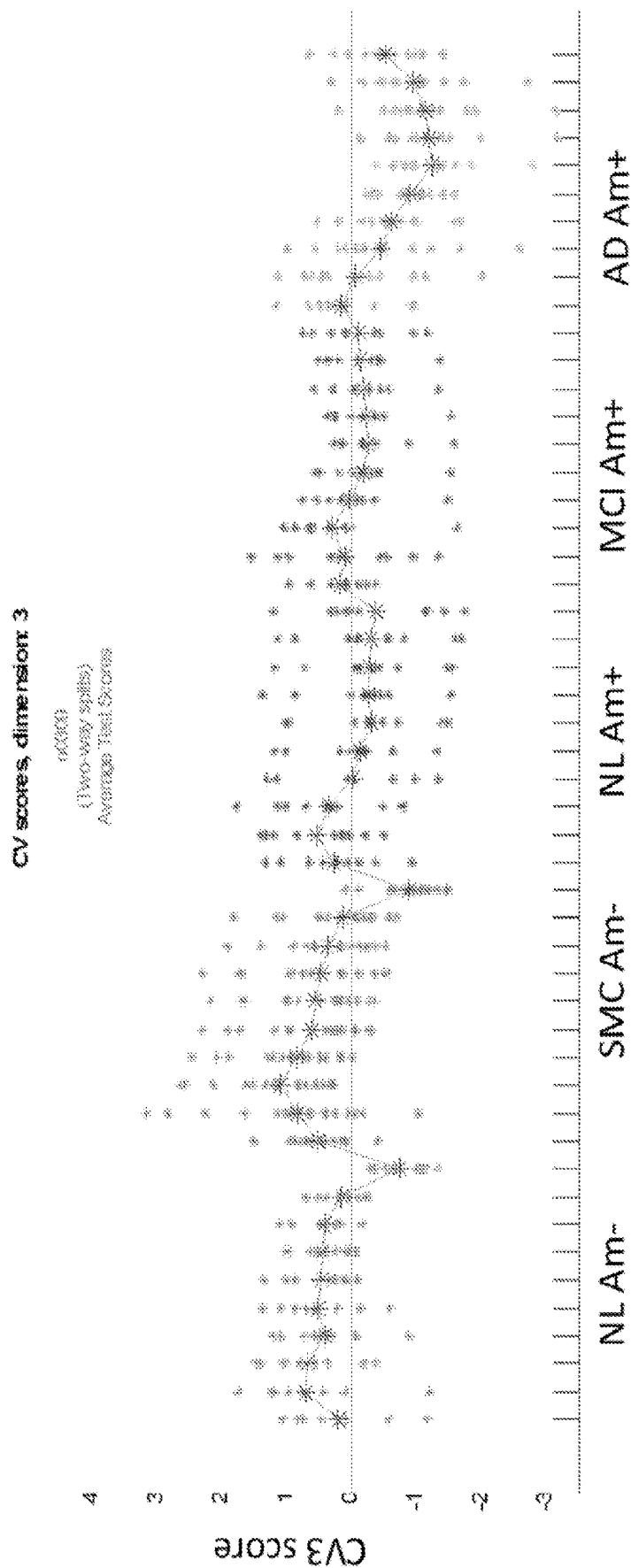
FIG. 13A is another graphical example showing CV scores for a classifier utilizing discrete and combined time frames.
Figure 13B:
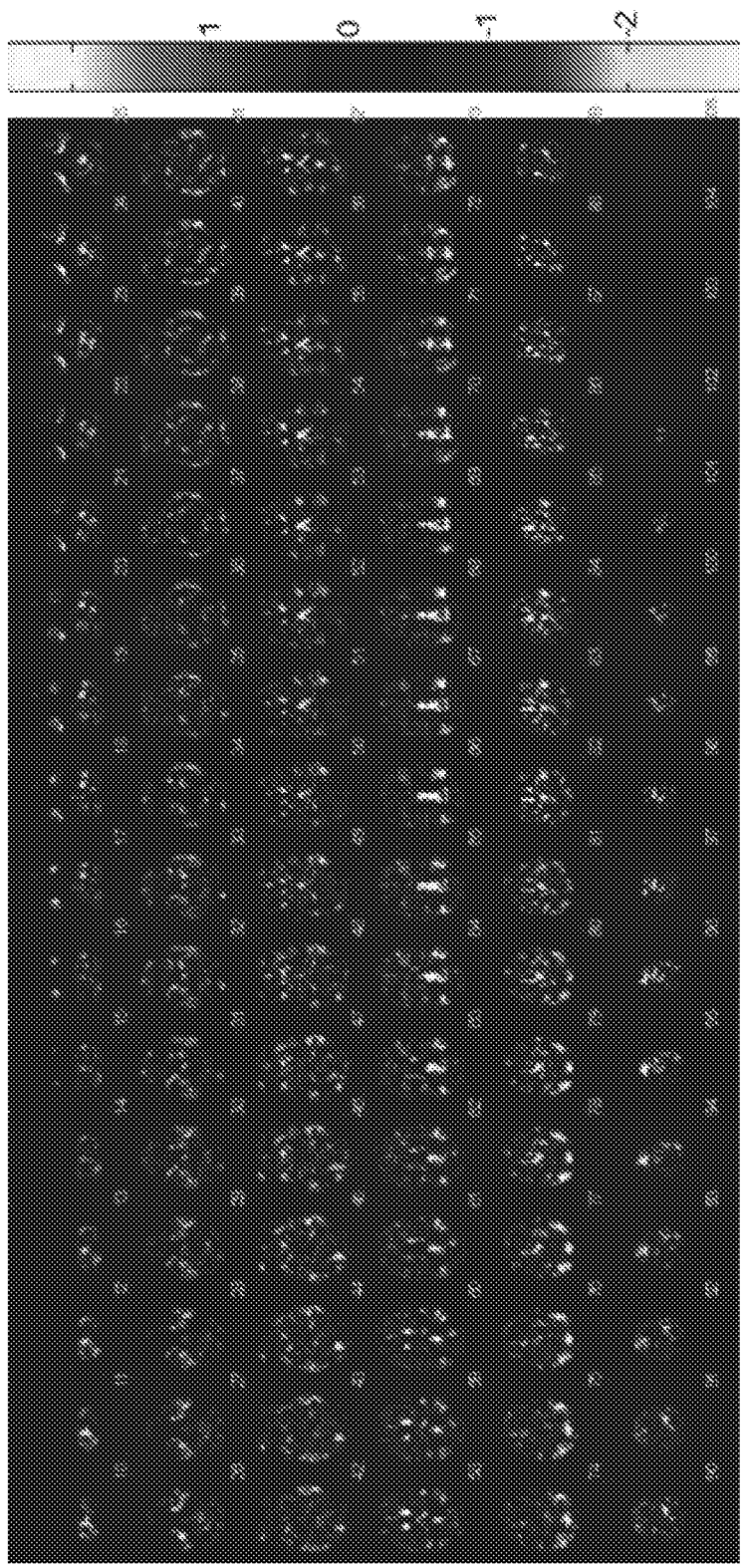
FIG. 13B is a graphical illustration showing image patterns corresponding to FIG. 13A.

Additional CVs, such as CV3, may provide potentially complementary information to further inform classification. For example, as shown in FIG. 13A, CV3 differs across the five groups with regard to both the vertical placement of the scores as well as the shape of the 11 frames comprising each time course of classes for the five groups. This may reflect a combination of functional differences (affecting the first few minutes, represented by the first 8 frames) as well as differences in amyloid burden (affecting the last frames), although the middle frames, and even all frames, contain some influence of both. FIG. 13B shows an eigenimage for CV3 of the combination discrete and summed time frame-classifier. This pattern, which the NL Am-subjects score most like and the AD Am+ subjects score most opposite to, is consistent with a pattern of AD-like neurodegeneration. Key regions of decline in AD Am+ include hippocampus, parietotemporal cortices, posterior cingulate, and precuneus (all shown in orange in this eigenimage), while cerebellum, occipital cortex, and sensorimotor cortex are relatively preserved (shown in blue for this eigenimage).

Figure 14A:
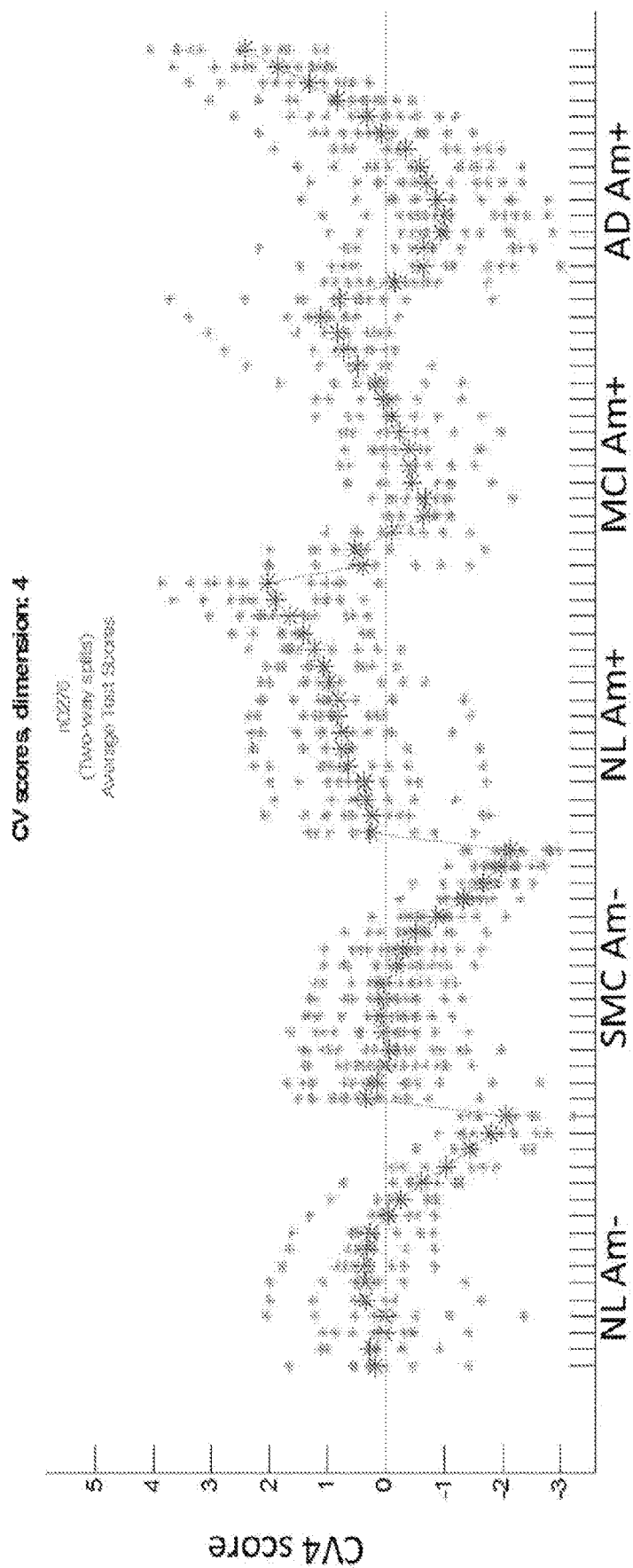
FIG. 14A is another graphical example showing CV scores for a classifier utilizing only discrete time frames.
Figure 14B:
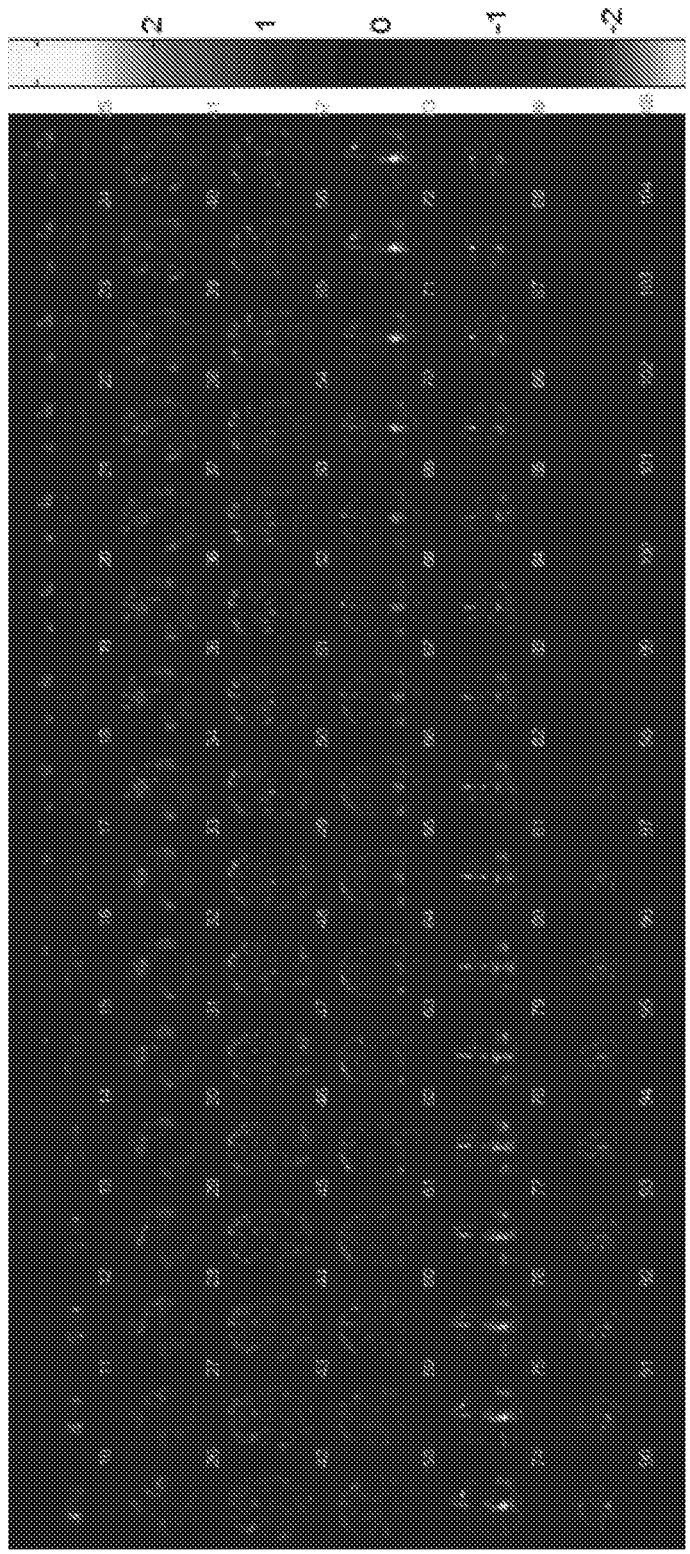
FIG. 14B is a graphical illustration showing image patterns corresponding to FIG. 14A.

Complementing the information regarding brain function or neurodegeneration most prevalent in the early frames, it is also possible to derive information regarding amyloid burden. In one implementation, amyloid burden may be classified using discrete time frames. In particular, whereas CV1 provide information regarding diagnostic state, as described, other CVs provide information regarding amyloid burden. For example, in FIG. 14A, it can be seen that the later frame slopes of the two amyloid negative classes decrease over time, while the slopes of the three amyloid positive classes increase over time, in the opposite direction. This creates opportunity to use either the absolute scores of the final frames, the slope of the last several frames, or another expression of the frame values to differentiate between amyloid negative and positive subjects. The associated eigenimage is shown in FIG. 14B. Note that the latter frames of the amyloid positive groups increase in the direction of pattern expression, which matches that of a typical amyloid positive distribution in the brain. In contrast, the latter frames of the amyloid negative groups move in the opposite direction.

Figure 15A:
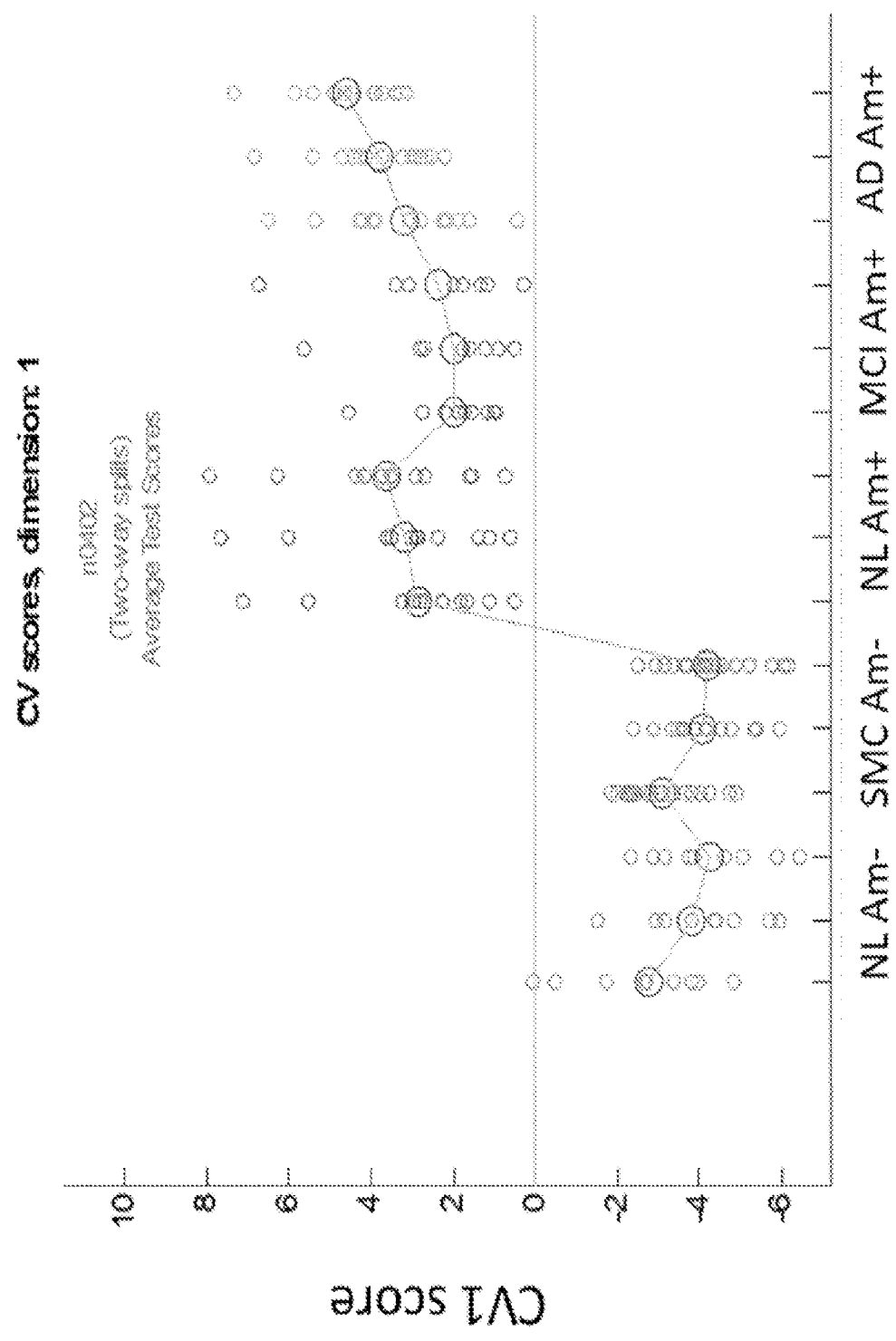
FIG. 15A is yet another graphical example showing CV scores for a classifier utilizing the last discrete time frames of an acquisition.
Figure 15B:
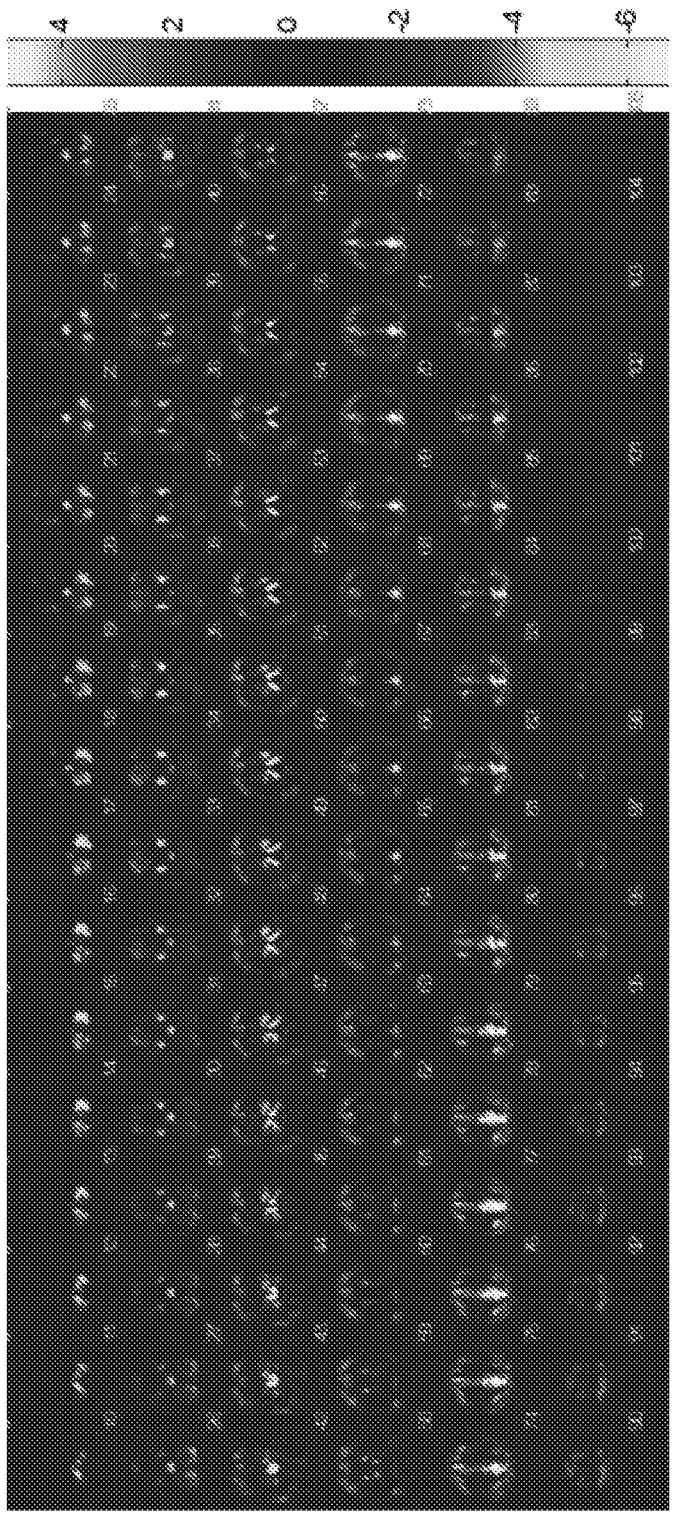
FIG. 15B is a graphical illustration showing image patterns corresponding to FIG. 15A.
Figure 15C:
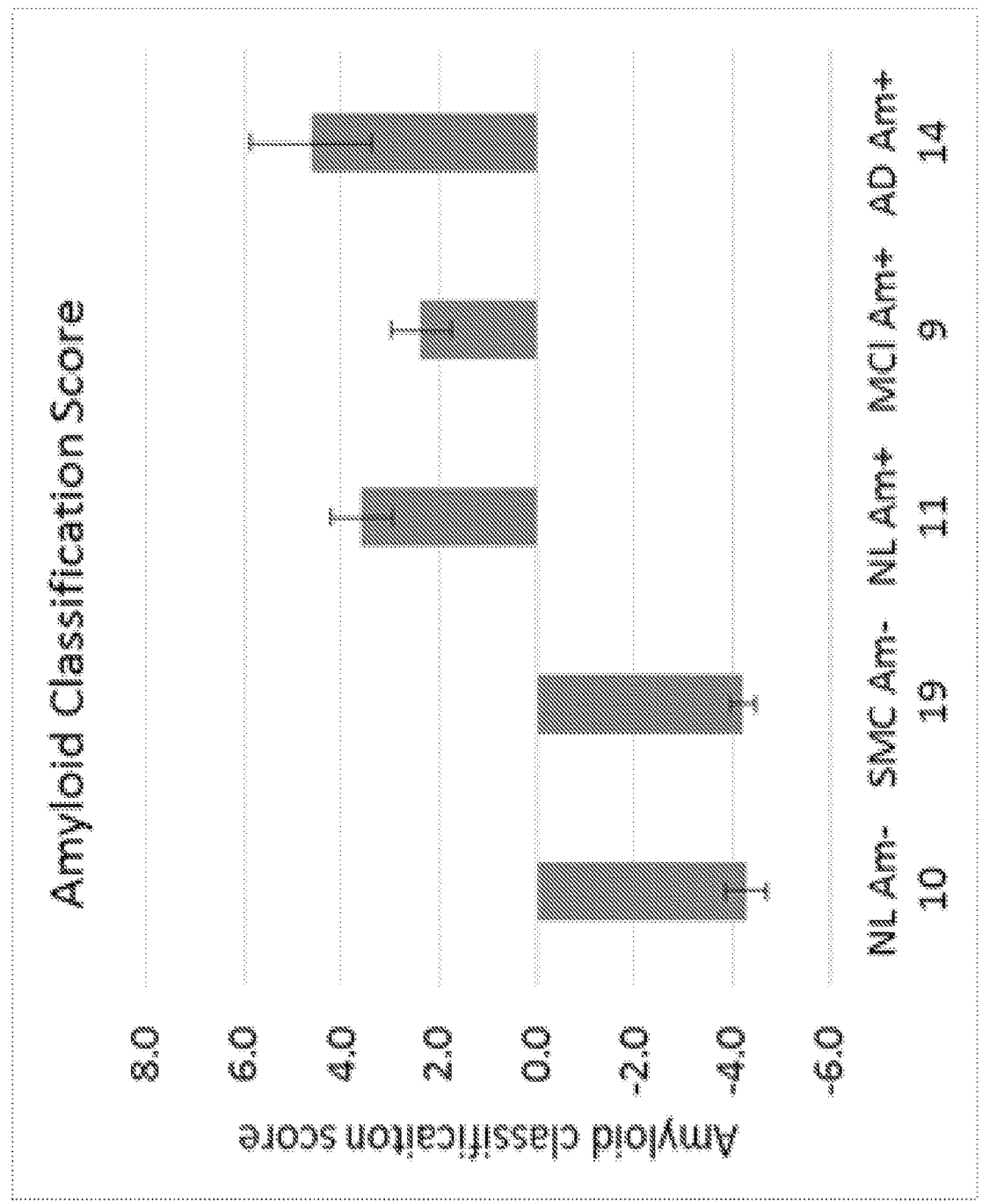
FIG. 15C is a graph showing mean CV values for the last frame of split half test, in accordance with aspects of the present disclosure.

In an alternative approach, only the last three timeframes (last 11 minutes of the 20 minute session) may be used, in a discrete manner. Split half test results for CV1 are shown in FIG. 15A, whereby the amyloid negative and amyloid positive groups are clearly separated. It can be noted that the CV1 for the last three frames is very similar to the last three frames contained within CV4 of the "all frames" classifier shown in FIG. 14A. FIG. 15B shows the respective eigenimage associated with the CV1 of the last 3 frame analysis of FIG. 15A. The increases are typical of amyloid deposition, while the decreases are consistent with those regions that do not accumulate amyloid. Of note is the low binding in white matter, which over time, but perhaps at a different kinetic rate, accumulates non-specific binding signal. FIG. 15 C shows the mean values and error bars associated with CV1 for the last frame of the split half test results using training groups.

Figure 16A:
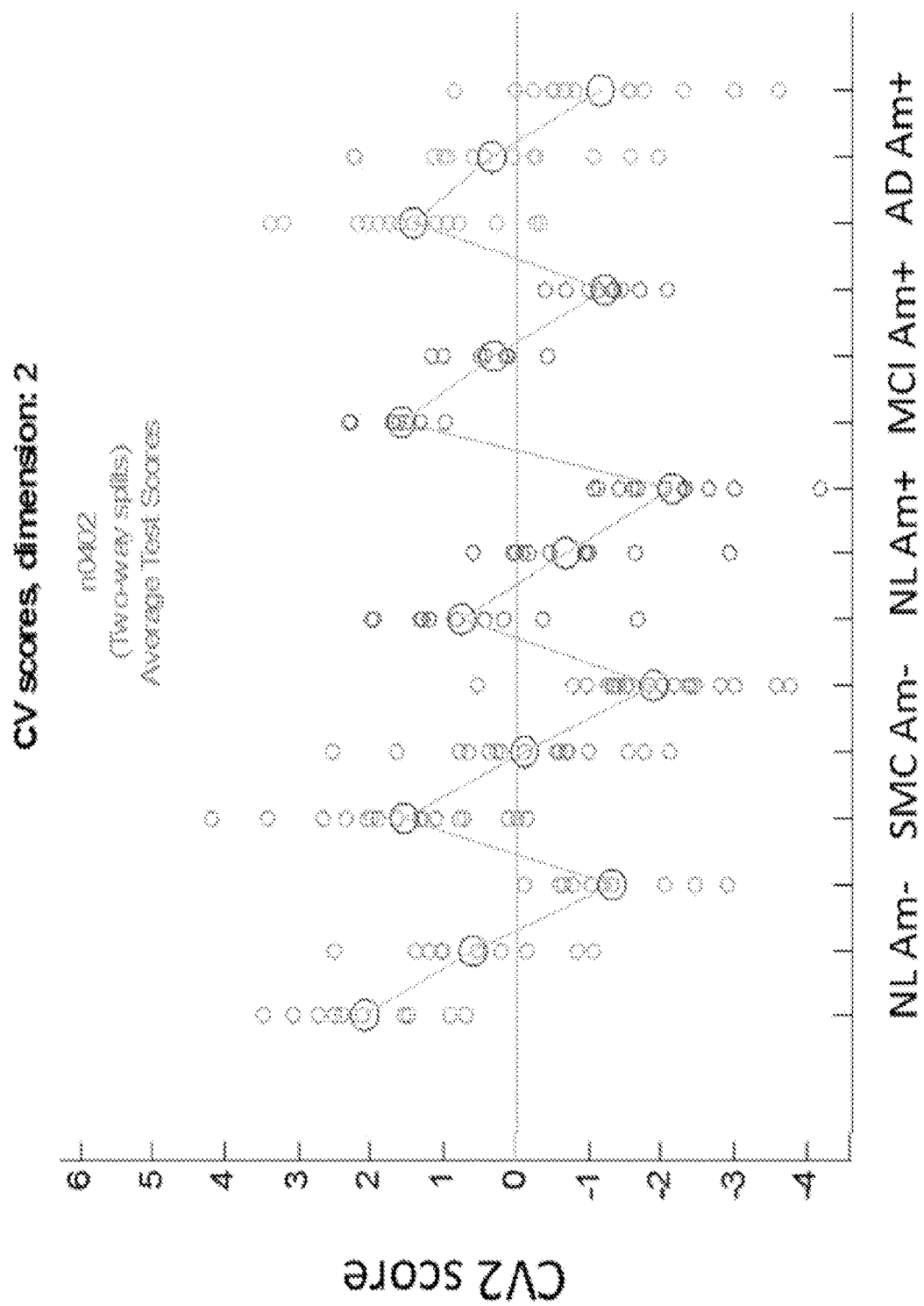
FIG. 16A is yet another graphical example showing CV scores for a classifier utilizing the last discrete time frames of an acquisition.
Figure 16B:
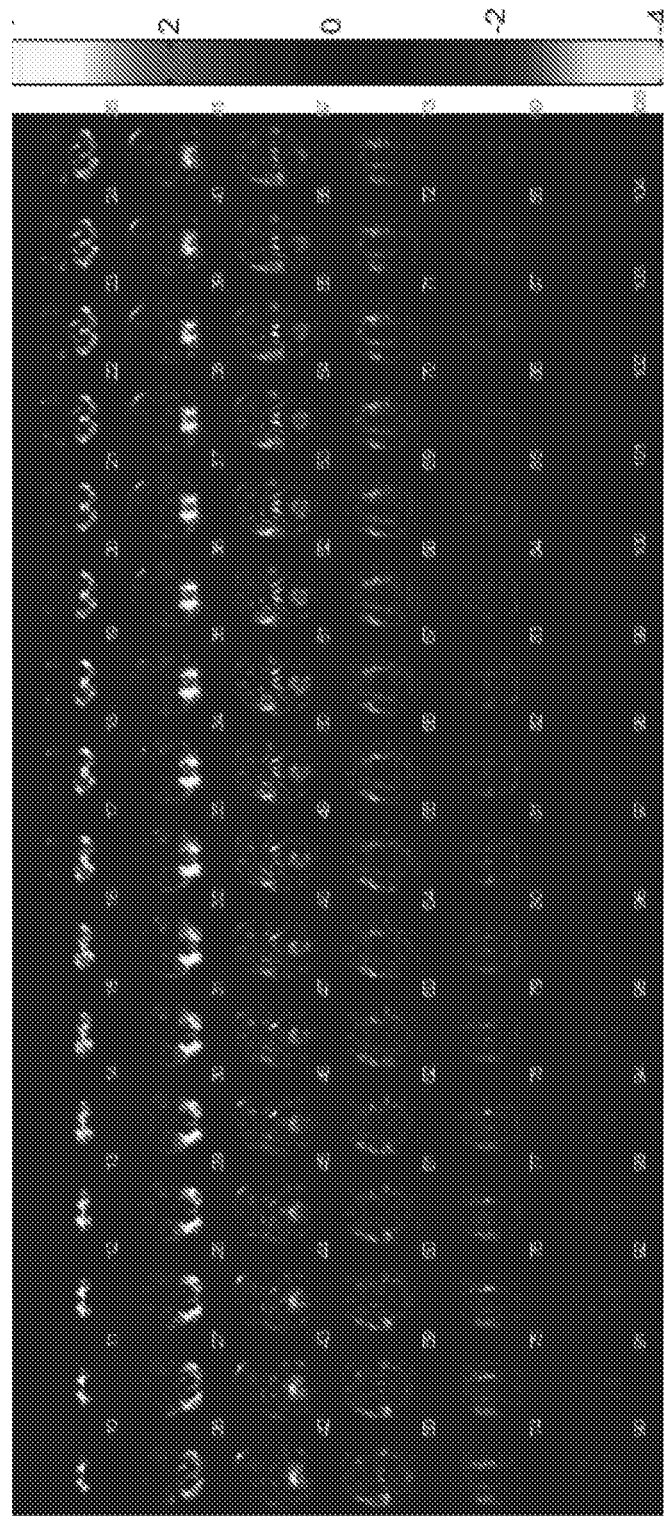
FIG. 16B is a graphical illustration showing image patterns corresponding to FIG. 16A.

As mentioned, associating frames within groups (i.e. individual frames are subclasses and diagnostic-amyloid groups are the main classes) can be a further approach that comes under the present disclosure. Of note is that CV2 of the last 3 frame analysis contains additional information involving both white matter as well as other regions that accumulate less amyloid. As such, FIGS. 16A and 16B show the CV plot and eigenimage for this CV, respectively. This appears to show the gradual clearance of tracer from cerebellum (since the eigenplots are headed in the opposite direction of the eigenimage, which shows increased signal), and gradual accumulation of tracer in white matter. These rates are likely different from the rates of tracer accumulation in gray matter as reflected in CV1.

In some aspects, the segregation of these components may be instrumental in identifying the critical patterns for amyloid identification. A Leave One Out ("LOO") approach may be utilized to provide validation. This iteratively leaves out each subject and creates a completely new classifier using N−1 subjects, and then scores the left out subject independently. The result is a complete set of scores generated by classifiers that were not trained using the left out subject in each case.

Although much more information may be obtained using multiple timeframes, it is possible to take only a single time frame (e.g. the frame acquired from 16-20 minutes) and use that an input to a classifier from which a discriminating pattern for amyloid negative vs. amyloid positive status is identified. For example, given the classifier pattern resulting from the three last timeframes, one could take only the last frame and compare it to the CV1 eigenimage derived from the last three timeframes, and still obtain scores that differentiate positive and negative burden.

Since the above-described classifiers were trained only on amyloid negative vs. positive groupings, they may not discriminate amyloid load within a positive or negative classification. In order to develop a classifier for amyloid burden measurement beyond positive/negative, classes having "tiers" of amyloid burden may as measured using their late frame scans may also be created. For example, an amyloid negative class, and classes whose late frame (50-70 minute) SUVRs are $1.1<x<1.2$, $1.2<x<1.3$, $1.3<x<1.4$, and so on, may be defined to enable an amyloid burden cascade classifier. Alternatively, one can use a continuous variable approach such as PLS.

Figure 17A:
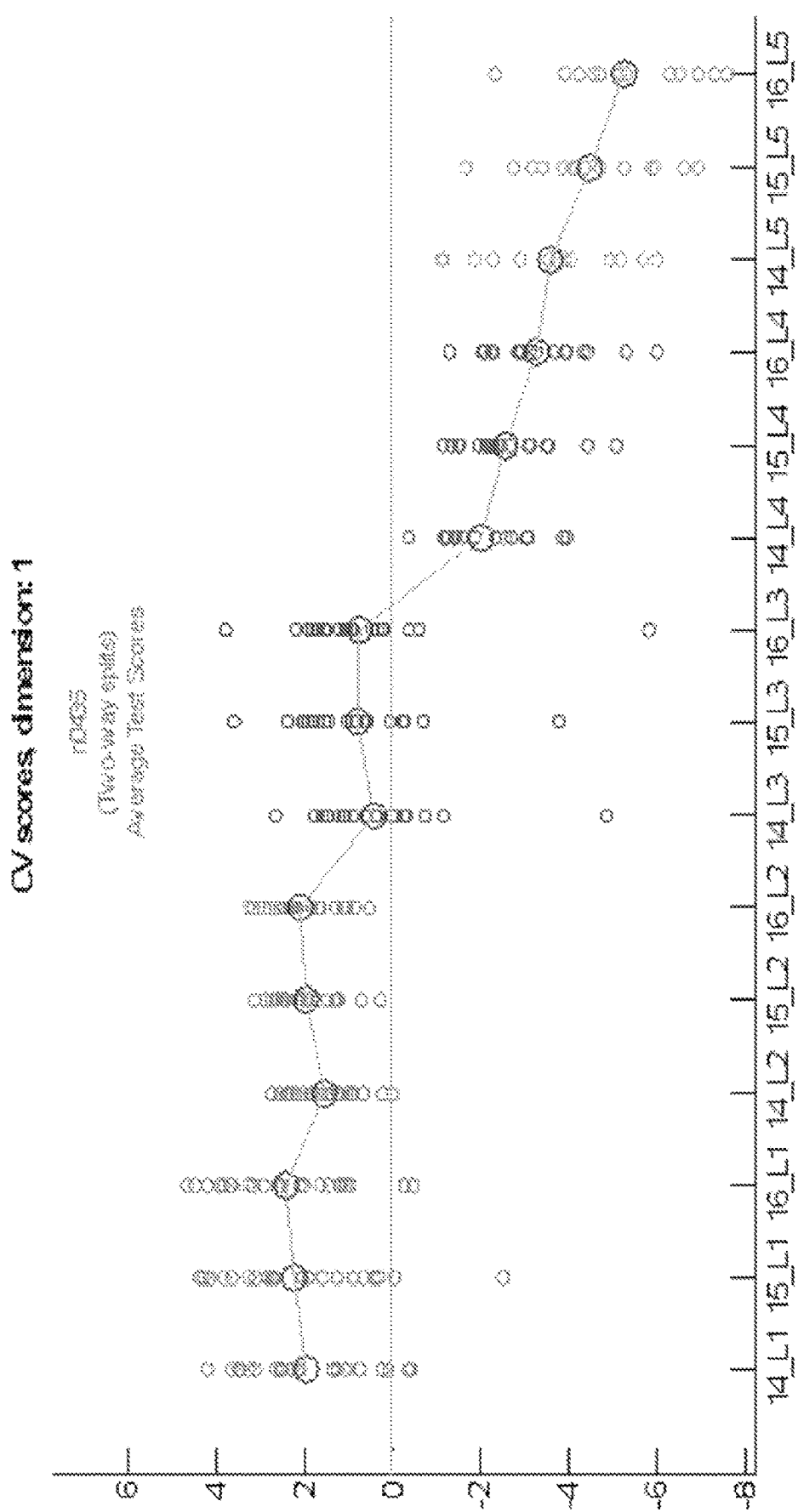
FIG. 17A is a graphical illustration showing amyloid burden cascade results, in accordance with aspects of the present disclosure.
Figure 17B:
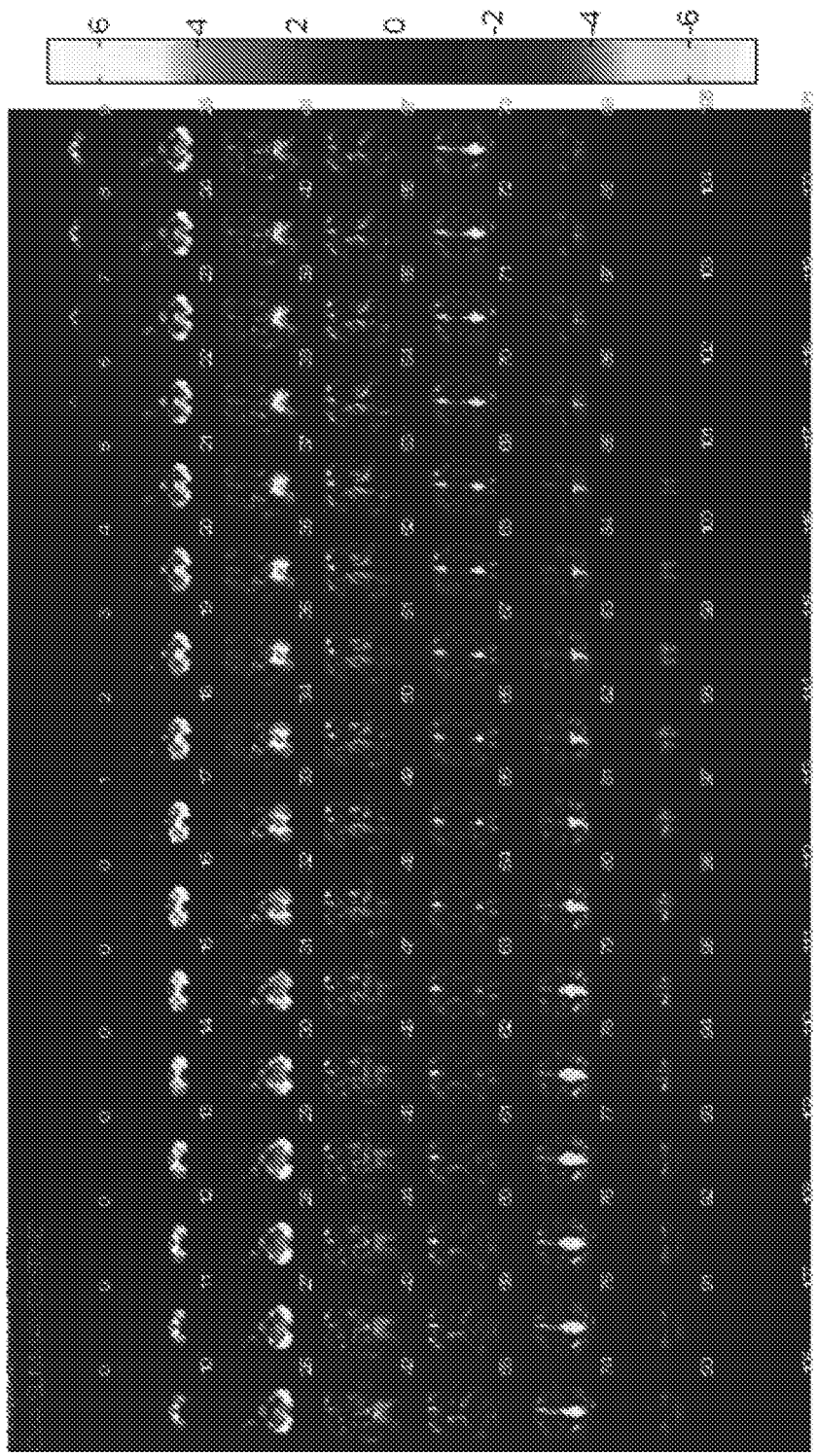
FIG. 17B is a graphical illustration showing image patterns corresponding to FIG. 17A.

Below is an example in which five strata were created based upon the amyloid SUVR values measured using standard late timeframes. However, the last three frames from the first twenty minutes (minutes 11 through 20) were inputted into the classifier. The result is a pattern (CV1) that reflects a "cascade" of amyloid accumulation (FIGS. 17A and 17B). In some aspects, other discrete frames can be used, as well as ways of using the shape or slope of each CV, or other properties, to enhance performance. This approach could also be used to compare longitudinal scans (scans from different visits, for example, 12 months apart). Each scan would be scored, and the scores compared.

The amyloid burden classifier can be extended to include (be trained on) different patterns of deposition that may reflect different diseases or cognitive trajectories. For example, cerebral amyloid angiopathy may associate with occipital amyloid without other regions as affected, and a classifier could be trained to discriminate this from AD like amyloid distributions. This could also be applied to tracers such as tau, where accumulation is variable across subjects and may correspond to different clinical phenotypes (symptom presentations).

The systems and methods described herein can also be applied to include co-varying or other inclusion of covariates such as subject age, gender, ApoE e4 status, and demographics. It is envisioned that a number of modifications to the above-described approaches may be possible. For instance, the comparison of the scan to a particular CV pattern may be used to create a more visually readable amyloid scan for reference. Also, slopes can be compared across CVs, and slope information can be used within a particular CV. In addition, CV information, particularly from early frames, can be used to adjust amyloid burden calculation for blood flow, as well as classification with alternative methods other than PCA. In some aspects, histograms may be used to catch increases in regional accumulation, and kinetic models may be created providing activity curve values for use into a classifier.

In some implementations of systems and methods described herein, a comparison of discrete values may also be performed, for instance, by comparing a particular set of regions from a last frame to a reference set of regions and intensities.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the disclosures described herein can be embodied within a form that does not provide all of the features and benefits set forth herein, as some features can be used or practiced separately from others. The scope of certain disclosures disclosed herein is indicated by the appended claims rather than by the foregoing description. All changes which come within the meaning and range of equivalency of the claims are to be embraced within their scope.

The invention claimed is:

1. A method for constructing a classifier for identifying a brain condition of a subject, the method comprising:
receiving image data obtained from a plurality of subjects, wherein the image data is acquired during an acquisition period following administration of at least one radioactive tracer and prior to the radioactive tracer reaching equilibrium;
defining a plurality of brain condition classes using the image data associated with one or more time frames during the acquisition period;
processing the image data to generate signatures corresponding to each of the plurality brain condition classes; and
constructing a classifier using the signatures.

2. The method of claim 1, wherein the image data includes at least one of a Positron Emission Tomography ("PET") data, or a Single Photon Emission Computed Tomography ("SPECT") data.

3. The method of claim 1, wherein the acquisition period is less than approximately 20 minutes after administration of at least one radioactive tracer.

4. The method of claim 1, wherein each of the one or more frames corresponds to a different brain condition class.

5. The method of claim 1, wherein each of the one or more time frames corresponds to a same brain condition class.

6. The method of claim 5, wherein the method further comprises combining image data associated with the one or more time frames to define the same brain condition class.

7. The method of claim 1, wherein the method further comprises performing a principal component analysis to generate the signatures.

8. The method of claim 1, wherein the method further comprises generating a report indicative of the signatures.

9. The method of claim 1, wherein the method further comprises applying the classifier to images acquired from a subject to identify a brain condition of the subject.

10. The method of claim 1, wherein the plurality of brain condition classes includes one or more of an Alzheimer's Disease class, a fronto-temporal dementia class, a Lewy Body Disease class, a vascular dementia class, a depression class, an amyloid class, a normal class, a cognitive impairment class, and subclasses thereof.

11. A method for identifying a brain condition of a subject, the method comprising:

receiving image data associated with a subject's brain;

constructing a classifier by defining a plurality of brain condition classes using the image data associated with one or more time frames acquired during an acquisition period, wherein each of the one or more frames corresponds to a different brain condition class;

applying the classifier to the image data to determine a degree to which the subject expresses one or more disease states;

determining a brain condition of the patient using the determined degree; and generating a report indicative of the brain condition of the patient.

12. The method of claim 11, wherein the image data includes amyloid Positron Emission Tomography ("PET") data.

13. The method of claim 11, wherein the constructing the classifier comprises:

defining a plurality of brain condition classes using images obtained from a plurality of subjects, wherein the images are associated with one or more time frames acquired during an acquisition period following administration of at least one radioactive tracer;

processing the images to generate signatures corresponding to each of the plurality brain condition classes; and constructing the classifier using the signatures.

14. The method of claim 13, wherein each of the one or more time frames corresponds to a same brain condition class.

15. The method of claim 14, wherein the method further comprises combining image data associated with the one or more time frames to define the same brain condition class.

16. The method of claim 13, wherein the method further comprises performing a principal component analysis to generate the signatures.

17. The method of claim 13, wherein the acquisition period is less than approximately 20 minutes.

18. A system for identifying a brain condition of a subject, the system comprising:

a processor configured to:

i) receive image data associated with a subject's brain;

ii) construct a classifier comprising signatures of different disease states using images acquired during an acquisition period following administration of at least one radioactive tracer and prior to the radioactive tracer reaching equilibrium;

iii) apply the classifier to the image data to determine a degree to which the subject expresses the disease states;

iv) determine a brain condition of the subject using the determined degree; and v) generate a report indicative of the brain condition of the subject.

19. The system of claim 18, wherein the image data includes at least one of a Positron Emission Tomography ("PET") data, or a Single Photon Emission Computed Tomography ("SPECT") data.

20. The system of claim 18, wherein the acquisition period is less than approximately 20 minutes.

21. The system of claim 18, wherein the processor is configured to construct the classifier by:

defining a plurality of brain condition classes using images obtained from a plurality of subjects;

processing the images to generate signatures corresponding to each of the plurality brain condition classes; and constructing a classifier using the signatures.

22. The system of claim 21, wherein generating the signatures includes applying a machine learning algorithm.

23. The system of claim 21, wherein each of the one or more frames corresponds to a different brain condition class.

24. The system of claim 21, wherein each of the one or more time frames corresponds to a same brain condition class.

25. The system of claim 24, wherein the processor is further configured to combine image data associated with the one or more time frames to define the same brain condition class.

26. The system of claim 18, wherein the processor is further configured to determine an amyloid burden using the classifier.

* * * * *